United States Patent
Kanai et al.

(10) Patent No.: US 8,099,160 B2
(45) Date of Patent: Jan. 17, 2012

(54) BODY FAT MEASURING DEVICE CAPABLE OF ACCURATELY MEASURING VISCERAL FAT AMOUNT

(75) Inventors: Hiroshi Kanai, Higashikurume (JP); Shojiro Oku, Kyoto (JP); Toshikazu Shiga, Otsu (JP); Yoshitake Oshima, Kyoto (JP); Nobuo Kubo, Kyoto (JP); Tetsuya Sato, Nishinomiya (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 932 days.

(21) Appl. No.: 12/088,622

(22) PCT Filed: Sep. 12, 2006

(86) PCT No.: PCT/JP2006/318041
§ 371 (c)(1),
(2), (4) Date: Mar. 28, 2008

(87) PCT Pub. No.: WO2007/043271
PCT Pub. Date: Apr. 19, 2007

(65) Prior Publication Data
US 2009/0247896 A1  Oct. 1, 2009

(30) Foreign Application Priority Data
Oct. 12, 2005  (JP) ................................ 2005-297399

(51) Int. Cl.
*A61B 5/05* (2006.01)
(52) U.S. Cl. ...................................... 600/547; 600/301
(58) Field of Classification Search .................. 600/547, 600/301
See application file for complete search history.

(56) References Cited

U.S. PATENT DOCUMENTS
6,978,170 B1 * 12/2005 Onda et al. .................... 600/547
2002/0111559 A1   8/2002 Kurata et al.
2003/0176808 A1 *  9/2003 Masuo ........................ 600/547
(Continued)

FOREIGN PATENT DOCUMENTS
EP   1 224 908   7/2002
(Continued)

OTHER PUBLICATIONS
International Search Report dated Dec. 19, 2006, directed to counterpart Application PCT/JP2006/318041 (1 page).
(Continued)

*Primary Examiner* — Max Hindenburg
*Assistant Examiner* — Renee Danega
(74) *Attorney, Agent, or Firm* — Morrison & Foerster LLP

(57) ABSTRACT

A body fat measuring device includes at least one pair of first electrodes to be disposed respectively at a first site and a second site sandwiching the abdomen of a subject, and an electrode group including a first abdomen electrode to be disposed at a surface of the abdomen of the subject. The first abdomen electrode includes a pair of second electrodes and a pair of third electrodes disposed in an alignment direction substantially perpendicular to a cross section of the abdomen. In a case where electric current is applied via the first electrodes, a first potential difference between electrodes of one predetermined pair included in the first abdomen electrode is detected. In a case where electric current is applied via the third electrodes, a second potential difference between the second electrodes is detected. Based on the detected two types of potential differences and physical data of the subject, the visceral fat amount of the subject is calculated.

20 Claims, 15 Drawing Sheets

U.S. PATENT DOCUMENTS

| | | |
|---|---|---|
| 2004/0059242 A1 | 3/2004 | Masuo et al. |
| 2004/0077969 A1* | 4/2004 | Onda et al. .................... 600/547 |
| 2005/0059903 A1* | 3/2005 | Izumi ............................ 600/547 |
| 2005/0107717 A1 | 5/2005 | Yamamoto et al. |

FOREIGN PATENT DOCUMENTS

| | | |
|---|---|---|
| EP | 1 554 976 | 7/2005 |
| JP | 7-079938 A | 3/1995 |
| JP | 11-123182 A | 5/1999 |
| JP | 2001-252257 | 9/2001 |
| JP | 2002-238870 A | 8/2002 |
| JP | 2002-369806 | 12/2002 |
| JP | 2005-103198 A | 4/2005 |
| WO | WO-02/065900 | 8/2002 |

OTHER PUBLICATIONS

Supplementary European Search Report mailed Nov. 17, 2010, directed to European Patent Application No. 06810058.5; 8 pages.

* cited by examiner

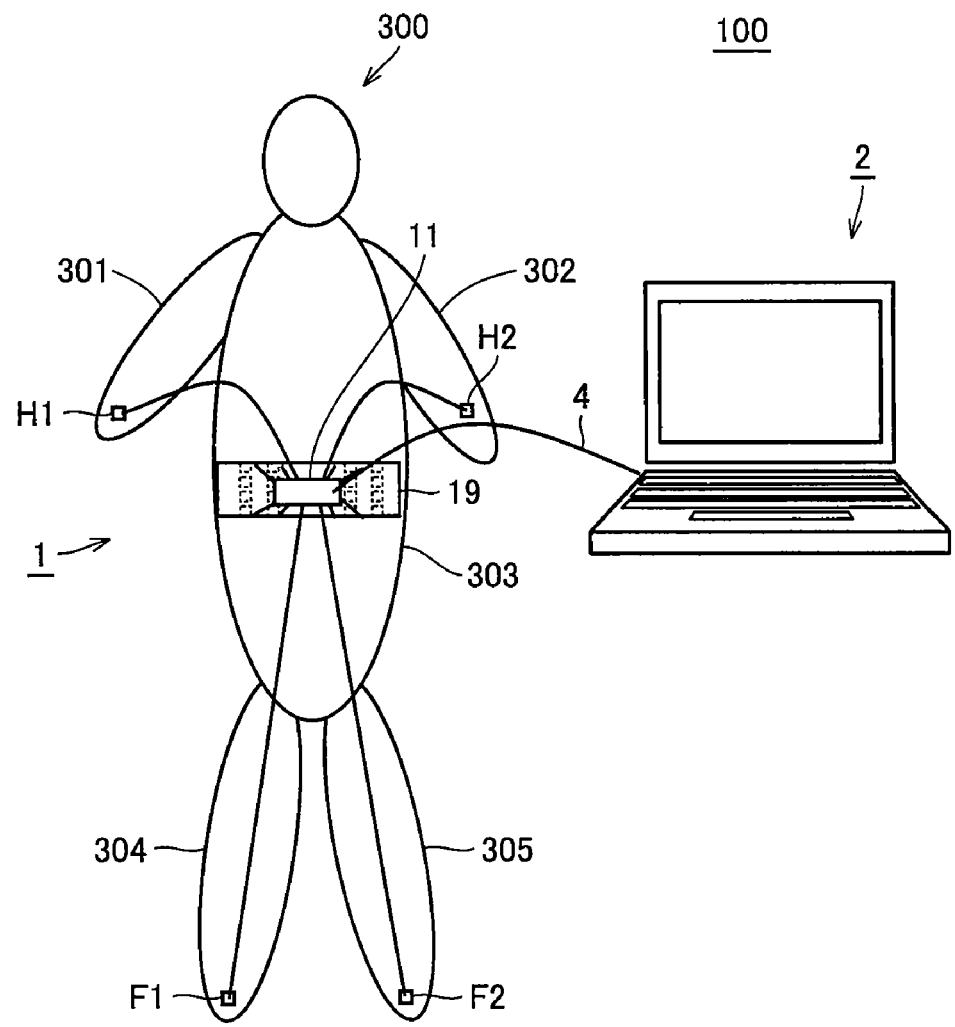

FIG.13A

| | | | |
|---|---|---|---|
| PATIENT ID | 012345 | WAIST LENGTH | 80cm |
| AGE | 35 | HEIGHT | 170cm |
| GENDER | MALE | WEIGHT | 80kg |

VISCERAL FAT AREA     110cm$^2$

SUBCUTANEOUS FAT AREA     90cm$^2$

BODY FAT PERCENTAGE     30%

FIG.13B

| | | | |
|---|---|---|---|
| PATIENT ID | 012345 | WAIST LENGTH | 80cm |
| AGE | 35 | HEIGHT | 170cm |
| GENDER | MALE | WEIGHT | 80kg |

VISCERAL FAT AREA     110cm$^2$

BODY FAT PERCENTAGE     30%

| | | | |
|---|---|---|---|
| VISCERAL FAT AREA | 110cm² | REFERENCE VALUE | 100cm² |
| SUBCUTANEOUS FAT AREA | 90cm² | | |
| BODY FAT PERCENTAGE | 30% | STANDARD VALUE | 10~20% |

BODY FAT MEASURING DEVICE CAPABLE OF ACCURATELY MEASURING VISCERAL FAT AMOUNT

REFERENCE TO RELATED APPLICATIONS

This application is a national stage application under 35 USC 371 of International Application No. PCT/JP2006/318041, filed Sep. 12, 2006, which claims the benefit of Japanese Patent Application No. 2005-297399, filed Oct. 12, 2005, the disclosures of which are hereby incorporated by reference.

TECHNICAL FIELD

The present invention relates to a body fat measuring device, a measuring unit, a body fat measuring program product and a method of controlling a body fat measuring device. In particular, the invention relates to a body fat measuring device capable of measuring a visceral fat amount of a subject using an impedance method, a measuring unit used for measuring a visceral fat amount, a body fat measuring program product for causing a computer to execute a body fat measuring process, and a method of controlling a body fat measuring device capable of measuring a visceral fat amount of a subject using an impedance method.

BACKGROUND ART

Conventionally, the visceral fat amount is actually measured using a tomogram of the abdomen taken with X-ray CT (Computed Tomography). Therefore, a problem here is that the visceral fat amount can be measured at only those medical institutions having X-ray CT facilities. While the MRI (Magnetic Resonance Imaging) can also be used to take a tomogram of the abdomen like that with the X-ray CT, large-sized facilities are necessary as well.

It has been proposed to measure the visceral fat amount without the necessity of large-sized facilities. For example, Japanese Patent Laying-Open No. 07-079938 (hereinafter Patent Document 1) discloses that the visceral fat amount is calculated based on specific physical data of a subject and the impedances of the whole body measured with electrodes arranged on the four limbs. Japanese Patent Laying-Open No. 2002-369806 (hereinafter Patent Document 2) discloses that the visceral fat amount is calculated based on physical data (such as waist length and gender) of a person whose measurement is taken and the voltage value of the abdomen. Further, Patent Document 2 discloses that a belt on which a plurality of electrodes are arranged in advance is wound around the abdomen of a subject so as to allow the electrodes to touch the abdomen.

Patent Document 1: Japanese Patent Laying-Open No. 07-079938

Patent Document 2: Japanese Patent Laying-Open No. 2002-369806

DISCLOSURE OF THE INVENTION

Problems to be Solved by the Invention

The device disclosed in Patent Document 1, however, estimates the visceral fat amount from the impedances of the four limbs, and it is not disclosed that the visceral fat amount is calculated using information about the subcutaneous fat amount as an important or necessary factor. Further, the device disclosed in Patent Document 2 flows current to the abdomen only. Therefore, the influence of the subcutaneous fat cannot be avoided resulting in a problem that the visceral fat amount cannot be measured accurately.

The present invention has been made to solve the above-described problems. An object of the invention is to provide a body fat measuring device capable of accurately measuring the visceral fat amount, a measuring unit, a body fat measuring program product, and a method of controlling a body fat measuring device.

Means for Solving the Problems

A body fat measuring device according to an aspect of the present invention includes: at least one pair of first electrodes to be disposed respectively at a first site and a second site that are a pair of different sites located away from an abdomen of a subject and located at respective positions sandwiching the abdomen; an electrode group including a first abdomen electrode to be disposed at a surface of the abdomen of the subject, the first abdomen electrode including a pair of second electrodes and a pair of third electrodes disposed in an alignment direction substantially perpendicular to a cross section of the abdomen, an applying portion for applying electric current to the subject via one of the pair of the first electrodes and the pair of the third electrodes; a detecting portion for detecting two types of potential differences respectively in a first case where the electric current is applied via the first electrodes and a second case where the electric current is applied via the third electrodes, the detecting portion detecting a first potential difference between electrodes of one predetermined pair included in the first abdomen electrode in the first case, and detecting a second potential difference between the second electrodes in the second case; and a visceral fat amount calculating portion for calculating a visceral fat amount of the subject based on the detected first and second potential differences and physical data of the subject.

Here, "abdomen" refers to a portion of the body trunk except for the thorax. Further, "sites located away from an abdomen" include: un upper limb including upper arm, lower arm, wrist, and fingers; the thorax located away from the diaphragm by a predetermined distance (approximately 10 cm for example); the upper body including shoulder, neck and head; and a lower limb including thigh, calf, ankle and toes.

Further, "visceral fat amount" refers to an amount concerning visceral fat and includes for example at least one of visceral fat weight, visceral fat area and visceral fat volume.

Preferably, the third electrodes are disposed at respective positions sandwiching the second electrodes in the alignment direction.

Preferably, the electrodes of the one predetermined pair are the second electrodes.

Alternatively, the electrodes of the one predetermined pair are preferably electrodes that are included in the first abdomen electrode and that are electrodes of a pair other than the pair of the second electrodes.

Further, preferably the third electrodes are disposed at respective positions sandwiching the second electrodes in the alignment direction, and the electrodes of the one predetermined pair are the third electrodes.

Preferably, the device further includes an impedance calculating portion for calculating two types of impedances based on the first potential difference and the second potential difference respectively, and the visceral fat amount calculating portion calculates the visceral fat amount based on the calculated two types of impedances and the physical data of the subject.

Preferably, the visceral fat amount calculating portion calculates the visceral fat amount using a predetermined correlation formula of a relation between the two types of impedances, the physical data and the visceral fat amount.

Further, preferably the body fat measuring device further includes a display portion for displaying the calculated visceral fat amount.

Preferably, the body fat measuring device further includes a subcutaneous fat amount calculating portion for calculating a subcutaneous fat amount of the subject based on the detected second potential difference and the physical data of the subject.

"Subcutaneous fat amount" refers to an amount concerning subcutaneous fat, and includes for example at least one of subcutaneous fat weight, subcutaneous fat area and subcutaneous fat volume.

Preferably, the physical data includes at least one of circumference of the abdomen, lateral width of the abdomen, thickness of the abdomen, height, and weight of the subject.

Here, "circumference of the abdomen" refers to the length of the circumference of a cross section of the abdomen and preferably refers to the length of the circumference of a cross section of a middle portion (around the navel) of the abdomen. It is also called waist length. "Lateral width of the abdomen" refers to the right-to-left width (length) of the abdomen and preferably refers to the right-to-left width of a middle portion of the abdomen. "Thickness of the abdomen" refers to the front-to-back thickness (length) of the abdomen and preferably refers to the front-to-back thickness of a middle portion of the abdomen.

Preferably, the first site and the second site include an upper limb and a lower limb respectively.

Preferably, the electrode group further includes a second abdomen electrode, the second abdomen electrode includes fourth electrodes and fifth electrodes disposed substantially parallel with the alignment direction and corresponding respectively to the second electrodes and the third electrodes, the applying portion further applies electric current to the subject via the fifth electrodes, the detecting portion further detects a third potential difference between the fourth electrodes in a case where electric current is applied via the fifth electrodes, and the visceral fat amount calculating portion calculates the visceral fat amount by averaging the second potential difference and the third potential difference.

Preferably, the first abdomen electrode further includes a pair of sixth electrodes, the detecting portion further detects a fourth potential difference between the sixth electrodes in the second case, and the visceral fat amount calculating portion calculates the visceral fat amount by averaging the second potential difference and the fourth potential difference.

Preferably, the first abdomen electrode includes a first surface contacting the surface of the abdomen and a second surface opposite to the first surface, and the body fat measuring device further includes a sheet material where the second surface is fixed.

Preferably, the sheet material includes positioning means corresponding to a navel position of the subject.

The positioning means is preferably a mark placed at a predetermined position of the sheet material.

Alternatively, the positioning means is preferably a hole opened at a predetermined position of the sheet material.

A measuring unit according to another aspect of the present invention is controlled by an operation unit calculating a visceral fat amount, for measuring a potential difference generated at a body surface of a subject in a state where electric current is applied to the subject, and the measuring unit includes: at least one pair of first electrodes to be disposed respectively at a first site and a second site that are a pair of different sites located away from an abdomen of the subject and located at respective positions sandwiching the abdomen; an electrode group including a first abdomen electrode to be disposed at a surface of the abdomen of the subject, the first abdomen electrode including a pair of second electrodes disposed in an alignment direction substantially perpendicular to a cross section of the abdomen and a pair of third electrodes disposed at respective positions sandwiching the second electrodes in the alignment direction; an applying portion for applying electric current to the subject via one of the pair of the first electrodes and the pair of the third electrodes based on a signal from the operation unit; a detecting portion for detecting two types of potential differences respectively in a first case where the electric current is applied via the first electrodes and a second case where the electric current is applied via the third electrodes, the detecting portion detecting a first potential difference between electrodes of one predetermined pair included in the first abdomen electrode in the first case, and detecting a second potential difference between the second electrodes in the second case; and a transmitting portion for transmitting to the operation unit data concerning the detected first and second potential differences.

A body fat measuring program product according to still another aspect of the present invention controls a measuring unit including an electric current applier for applying electric current to a subject and a detector for detecting a potential difference generated at a body surface of the subject in a state where the electric current is applied to the subject, for causing a computer to execute a body fat measuring process based on a result of measurement by the measuring unit, and the body fat measuring program product causes the computer to execute the steps of: causing the electric current applier to apply electric current via at least one pair of out-of-abdomen electrodes disposed at respective sites that are a pair of different sites located away from an abdomen of the subject and located at respective positions sandwiching the abdomen; causing the detector to detect a first potential difference between electrodes of one predetermined pair among four electrodes disposed at a surface of the abdomen and disposed in an alignment direction substantially perpendicular to a cross section of the abdomen, in a state where the electric current is applied via the out-of-abdomen electrodes; causing the electric current applier to apply electric current via a pair of first abdomen electrodes located on an outer side among the four electrodes; causing the detector to detect a second potential difference between second abdomen electrodes of a pair located on an inner side among the four electrodes, in a state where the electric current is applied via the first abdomen electrodes, obtaining the detected first and second potential differences; and calculating a visceral fat amount of the subject based on the obtained first and second potential differences and physical data of the subject.

A method of controlling a body fat measuring device according to a further aspect of the present invention controls a measuring unit including an electric current applier for applying electric current to a subject and a detector for detecting a potential difference generated at a body surface of the subject in a state where the electric current is applied to the subject, for causing the body fat measuring device including the measuring unit to execute a body fat measuring process, and the method includes the steps of: causing the electric current applier to apply electric current via at least one pair of out-of-abdomen electrodes disposed at respective sites that are a pair of different sites located away from an abdomen of the subject and located at respective positions sandwiching the abdomen; causing the detector to detect a first potential difference between electrodes of one predetermined pair among four electrodes disposed at a surface of the abdomen and disposed in an alignment direction substantially perpendicular to a cross section of the abdomen, in a state where the electric current is applied via the out-of-abdomen electrodes; causing the electric current applier to apply electric current via a pair of first abdomen electrodes located on an outer side among the four electrodes; causing the detector to detect a second potential difference between second abdomen electrodes of a pair located on an inner side among the four electrodes, in a state where the electric current is applied via the first abdomen electrodes; obtaining the detected first and second potential differences; and calculating a visceral fat amount of the subject based on the obtained first and second potential differences and physical data of the subject.

EFFECTS OF THE INVENTION

According to the present invention, the visceral fat amount is calculated based on two types of potential differences between electrodes that are disposed in an alignment direction substantially perpendicular to a cross section of the abdomen. Thus, the accurate visceral fat amount can be measured.

BRIEF DESCRIPTION OF THE DRAWINGS

FIG. 4 illustrates how the body fat of a subject is measured using the body fat measuring device in the first embodiment of the present invention.

FIG. 13A is a first diagram showing an example where data concerning a subject is displayed in addition to measurement results.

FIG. 13B is a second diagram showing an example where data concerning a subject is displayed in addition to measurement results.

Figure 1:
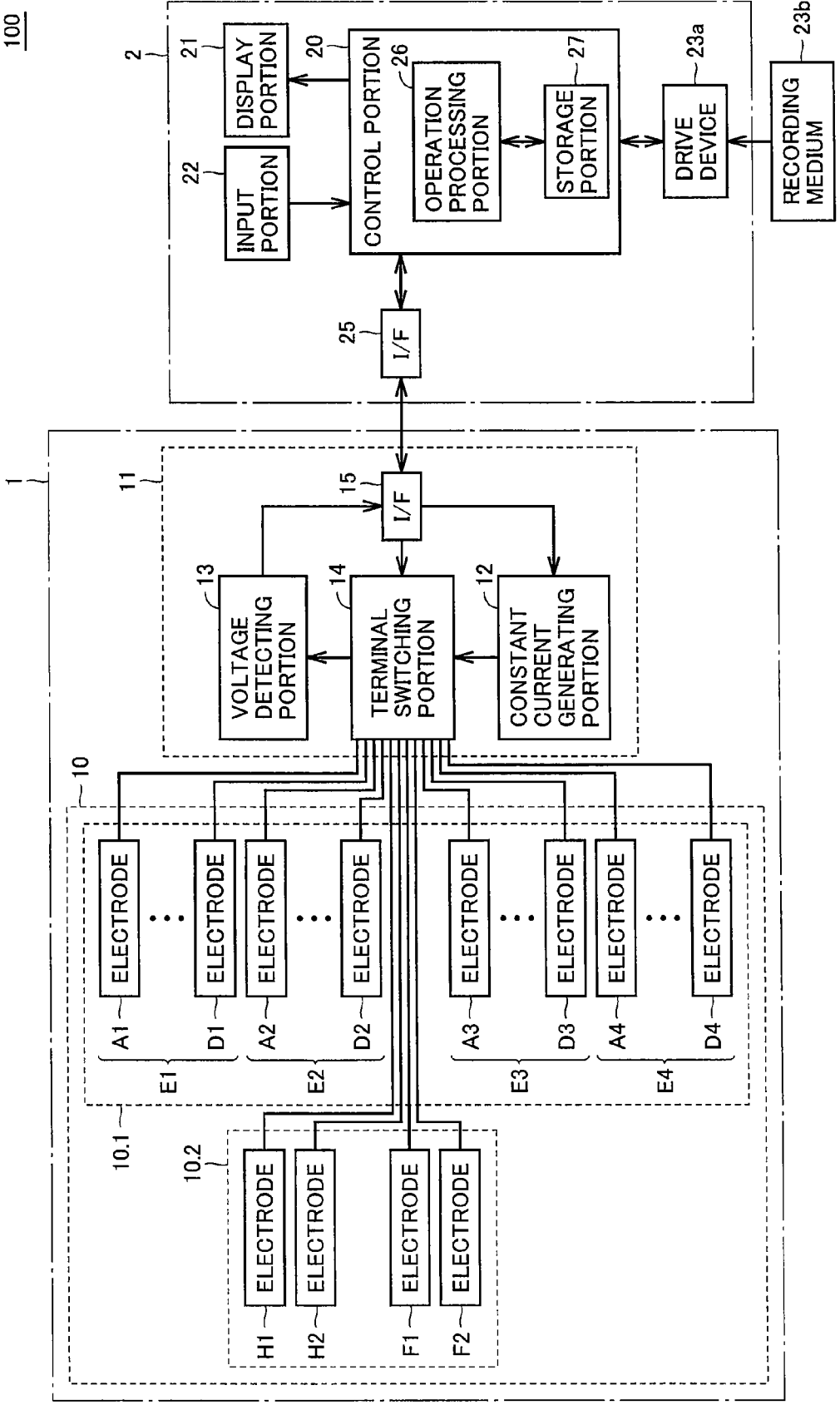
FIG. 1 is a block diagram showing a configuration of a body fat measuring device in a first embodiment of the present invention.

DESCRIPTION OF THE REFERENCE SIGNS 1 measuring unit, 2 operation unit, 3, 3A measurement operation device, 4 wire, 10 electrode portion, 10.1 abdomen electrode portion, 10.2 four-limb electrode portion, 11 measurement processing device, 12 constant current generating portion, 13 voltage detecting portion, 14 terminal switching portion, 19, 19A electrode sheet, 20 control portion, 21 display portion, 22 input portion, 23*b* recording medium, 23*a* drive device, 26 operation processing portion, 27 storage portion, 29 communication device, 31 measurement start key, 32 measurement stop key, 33 hinge, 51 adhesive sheet, 61A sheet material payer, 61B sheet material layer, 62 adhesive material layer, 63 electrode base layer, 64 electrode layer, 65 gel layer, 71 battery, 100, 200 body fat measuring device, 261 impedance calculating portion, 262 body fat calculating portion, 262A visceral fat amount calculating portion, 262B subcutaneous fat amount calculating portion, 262C body fat amount calculating portion, 300 subject, 301 right arm, 302 left arm, 303 abdomen, 304 right leg, 305 left leg, A1, B1, C1, D1, A2, B2, C2, D2, A3, B3, C3, D3, A4, B4, C4, D4, H1, H2, F1, F2 electrode, E1, E2, E3, E4 abdomen electrode row, PS1 mark, PS2 hole

BEST MODES FOR CARRYING OUT THE INVENTION

Embodiments of the present invention will be described in detail with reference to the drawings. In the drawings, like or corresponding components are denoted by like reference characters.

First Embodiment

Configuration and External Appearance of Body Fat Measuring Device

As to configuration:

Referring to FIG. 1, a body fat measuring device 100 includes a measuring unit 1 and an operation unit 2. Measuring unit 1 includes an electrode portion 10 and a measurement processing device 11. Measuring unit 1 is a device controlled by operation unit 2 to measure a potential difference generated at a body surface of a subject in the state where electric current is applied to the subject.

Electrode portion 10 includes an abdomen electrode portion 10.1 and a four-limb electrode portion 10.2. Four-limb electrode portion 10.2 includes electrodes H1, H2 to be disposed at the upper limbs of the subject and electrodes F1, F2 to be disposed at the lower limbs of the subject. Although it is described here that two pairs of electrodes H1, H2 and F1, F2 are included, at least one pair of electrodes may be included. Therefore, a pair of one of electrodes H1 and H2 disposed at the upper limbs and one of electrodes F1 and F2 disposed at the lower limbs may be included. Further, although it is described here that at least one electrode is disposed at each of the upper limbs and the lower limbs, the sites where the electrodes are disposed are not limited to the pair of upper limb and the lower limb, and the electrodes may be disposed at a pair of different sites that are located away from the abdomen of the subject and located at respective positions sandwiching the abdomen.

Abdomen electrode portion 10.1 includes four abdomen electrode rows E1, E2, E3, E4. Abdomen electrode row E1 includes four electrodes A1, B1, C1, D1 and abdomen electrode row E2 includes four electrodes A2, B2, C2, D2. Abdomen electrode row E3 includes four electrodes A3, B3, C3, D3 and abdomen electrode row E4 includes four electrodes A4, B4, C4, D4. Although it is supposed here that abdomen electrode portion 10.1 includes four abdomen electrode rows E1, E2, E3, E4, at least one abdomen electrode row may be included.

In the present embodiment, measuring unit 1 further includes a sheet material described hereinlater, and abdomen electrode portion 10.1 is fixed to the sheet material in advance. An example of specific arrangement of each abdomen electrode row will be detailed hereinlater.

Measurement processing device 11 includes a constant current generating portion 12 for generating a high-frequency constant current (for example, 50 kHz, 500 μA), a voltage detecting portion 13 for detecting a potential difference between electrodes of one pair that is energized, a terminal switching portion 14 for selecting from a plurality of electrodes included in electrode portion 10 electrodes for current and electrodes for voltage, and an I/F 15 for making communication with operation unit 2.

Terminal selecting portion 14 is connected to constant current generating portion 12 and voltage detecting portion 13 and connected to each electrode included in electrode portion 10. Terminal switching portion 14 is controlled by operation unit 2 to switch electrodes and select at least one pair of electrodes for current from the electrodes included in electrode portion 10. Thus, the constant current generated by constant current generating portion 12 is applied via the selected electrodes to the subject. Terminal switching portion 14 is also controlled by operation unit 2 to switch electrodes and select a pair of electrodes for voltage from the electrodes included in electrode portion 10. Thus, voltage detecting portion 13 can detect a potential difference between the electrodes selected each time. The information about the detected potential difference is supplied via I/F 15 to operation unit 2. Terminal switching portion 14 is configured for example with a plurality of switches.

Here, constant current generating portion 12 and terminal switching portion 14 allow current to be applied to the subject via any of two pairs of electrodes H1, H2, F1, F2, a pair of electrodes A1, D1, a pair of electrodes A2, D2, a pair of electrodes A3, D3 and a pair of electrodes A4, D4. Further, voltage detecting portion 13 and terminal switching portion 14 allow the potential difference to be detected between each of the paired electrodes B1, C1, paired electrodes B2, C2, paired electrodes B3, C3 and paired electrodes B4, C4.

In the present embodiment, although terminal switching portion 14 is connected to both of constant current generating portion 12 and voltage detecting portion 13 to select both of the electrodes for current and the electrodes for voltage, the configuration is not limited to the above-described one. For example, instead of terminal switching portion 14, a first switching portion connected to constant current generating portion 12 for selecting only the electrodes for current and a second switching portion connected to voltage detecting portion 13 for selecting only the electrodes for voltage may be provided.

Further, in the present embodiment, although the electrodes for current and the electrodes for voltage are selected via terminal switching portion 14, the configuration may not include terminal switching portion 14. In this case, for example, a current generator may be provided for each pair of electrodes serving as the electrodes for current and operation unit 2 may control each current generator. Thus, the electrodes for current can be switched successively without using terminal switching portion 14. Similarly, a voltage detector may be provided for each pair of electrodes serving as the electrodes for voltage and operation unit 2 may control each voltage detector. In this way, without using terminal switching portion 14, the electrodes for voltage can be switched successively.

Operation unit 2 includes a control portion 20 performing overall control of body fat measuring device 100, a display portion 21 for displaying results of the measurement for example, an input portion 22 for entering subject data as described hereinlater, a drive device 23a capable of reading and writing data recorded on recording medium 23b, and an I/F 25 for communicating with measurement processing device 11.

Here, "subject data" refers to data concerning the body of the subject including at least physical data, and includes for example, at least one of the waist length (the circumference of the abdomen), lateral width of the abdomen, thickness of the abdomen, height, weight, age, and gender. In the present embodiment, the physical data is described as the data corresponding to the waist length.

Here, the physical data is not limited to the waist length and may be other data concerning the abdomen (such as lateral width of the abdomen, thickness of the abdomen) or data concerning the whole body (such as height, weight). The physical data is not limited to a piece of data and may include two or more pieces of data.

Control portion 20 includes an operation processing portion 26 for performing various types of operation and a storage portion 27 for storing a program and data. Here, a body fat measuring program recorded on recording medium 23b may be read by drive device 23a and a body fat measuring process as described below may be performed.

Display portion 21 is configured with a liquid crystal for example. Input portion 22 is configured for example with a plurality of keys that can be pressed by a user.

Here, operation unit 2 may be a commonly used PC (personal computer).

Figure 2:
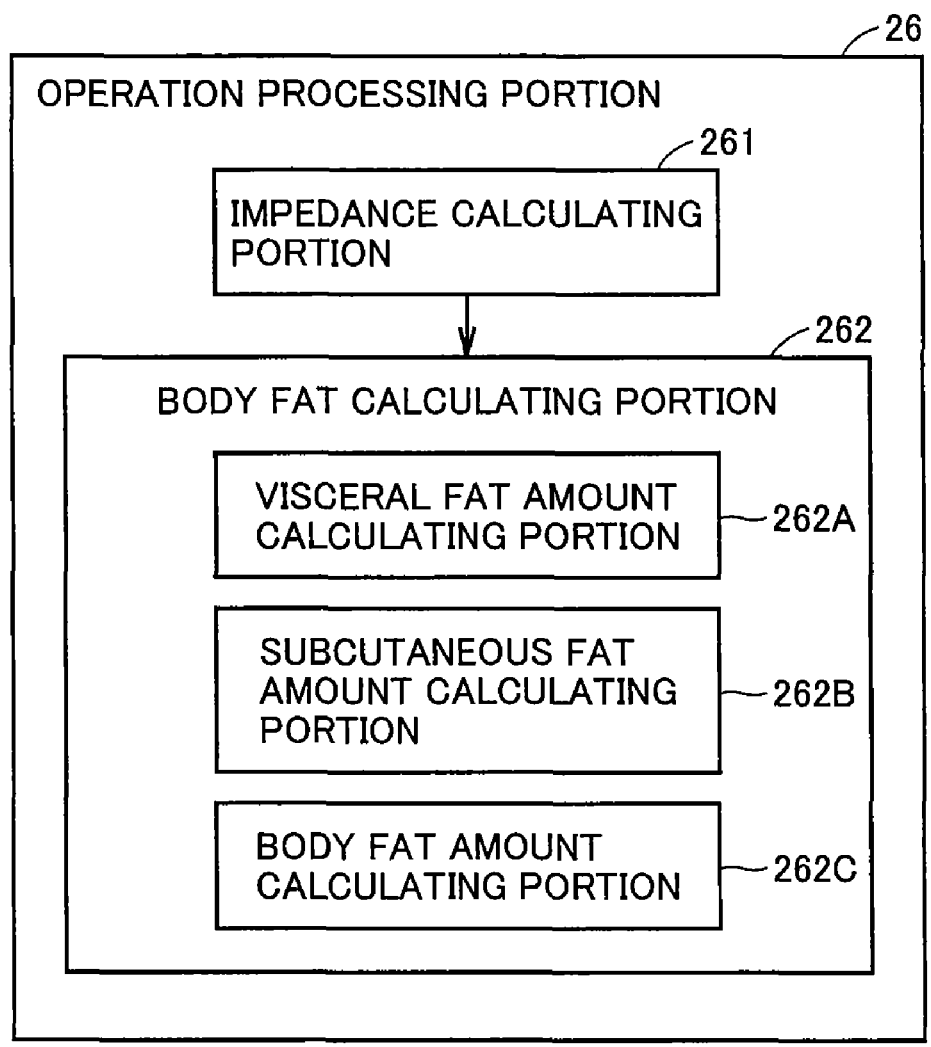
FIG. 2 is a block diagram showing a functional configuration of an operation processing portion.

Referring next to FIG. 2, in the present embodiment, operation processing portion 26 includes an impedance calculating portion 261 for calculating two types of impedances of the subject and a body fat calculating portion 262 for calculating the body fat of the subject. In the present embodiment, the body fat includes at least an amount of visceral fat and preferably includes an amount of subcutaneous fat and an amount of body fat in addition to an amount of visceral fat. "Body fat amount" refers to an amount relevant to the body fat and includes for example at least one of the body fat weight, the body fat volume and the body fat percentage. Here, the body fat amount includes an amount of visceral fat and an amount of subcutaneous fat.

Impedance calculating portion 261 calculates two types of impedances based on a current value generated by constant current generating portion 12 and two type of potential differences obtained from measurement processing device 11 via I/F 25. One of the two types of impedances is an impedance reflecting the fat amount of the whole of a cross section of the abdomen of the subject (namely the sum of the visceral fat amount and the subcutaneous fat amount). The other one is an impedance reflecting the subcutaneous fat amount of a cross section of the abdomen of the subject. In the following description, the impedance reflecting the total fat amount is represented by "Zt" and the impedance reflecting the subcutaneous fat amount is represented by "Zs".

Body fat calculating portion 262 includes a visceral fat amount calculating portion 262A for calculating the visceral fat amount, a subcutaneous fat amount calculating portion 262B for calculating the subcutaneous fat amount and a body fat amount calculating portion 262C for calculating the body fat amount.

Visceral fat amount calculating portion 262A calculates the visceral fat amount, for example, the visceral fat area (unit: cm$^2$) of the subject based on the calculated two types of impedances Zt, Zs and the physical data (waist length) of the subject. Specifically, a relation between the two types of impedances Zt, Zs and the waist length and the visceral fat amount of the subject is represented by formula (1) as shown below which is used to calculate visceral fat area Sv.

$$Sv=a*W^2-b*(1/Zt)-c*W*Zs-d \quad (1)$$

(where a, b, c, d: factor, W: waist length)

Subcutaneous fat amount calculating portion 262B calculates the subcutaneous fat amount, for example, the subcutaneous fat area (unit: cm$^2$) of the subject based on the calculated impedance Zs and the physical data (waist length) of the subject. Specifically, for example, a relation between impedance Zs and the waist length and subcutaneous fat amount of the subject is represented by following formula (2) which is used to calculate subcutaneous body area Ss.

$$Ss=e*W*Zs+f \quad (2)$$

(where e, f: factor, W: waist length)

Body fat amount calculating portion 262C calculates the body fat amount, for example, body fat percentage (%) of the subject based on the calculated impedance Zt and at least a piece of data (weight for example) included in the subject data. Specifically, the body fat percentage is calculated using following formula (3) based on fat free mass FFM and the weight of the subject.

$$\text{Body fat percentage}=(Wt-FFM)/Wt*100 \quad (3)$$

(where Wt: weight)

Fat free mass FFM (unit: kg) is calculated using following formula (4) representing the relation between impedance Zt and a piece of data (height for example) included in the subject data and the fat free mass.

$$FFM=i*H^2/Zt+j \quad (4)$$

(where i, j: factor, H: height)

Correlation formulas (1), (2) and (4) as described above are defined by the relation with a reference measured for example with the MRI. Such correlation formulas may be defined for each age and/or gender.

Figure 3A:
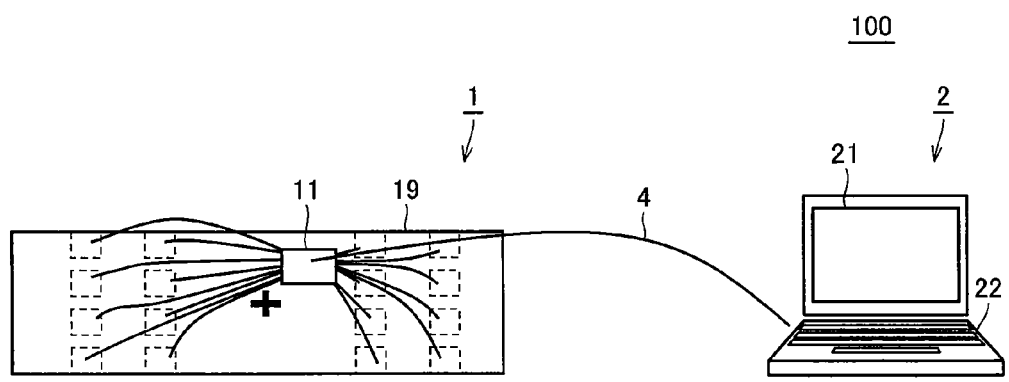
FIG. 3A is a first diagram showing an external appearance of the body fat measuring device in the first embodiment of the present invention.
Figure 3B:
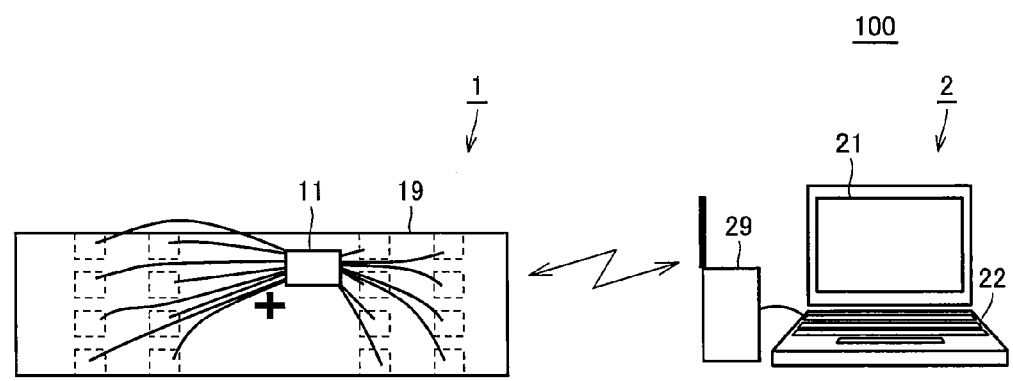
FIG. 3B is a second diagram showing an external appearance of the body fat measuring device in the first embodiment of the present invention.

As to external appearance:

Here, in FIGS. 3A and 3B, four-limb electrode portion 10.2 is not shown.

As shown in FIG. 3A, measurement processing device 11 and operation unit 2 perform wired communication via a wire 4 for example. Measurement processing device 11 is disposed on a surface (surface opposite to the surface touching the abdomen of the subject) of an electrode sheet 19. Electrode sheet 19 refers to abdomen electrode portion 10.1 and a sheet material integrated into the electrode sheet.

Thus, measurement processing device 11 disposed on electrode sheet 19 and operation unit 2 are provided as separate portions and accordingly measurement processing device 11 can be made compact.

Here, in the present embodiment, electrode sheet 19 is described as the one that is substantially rectangular in shape.

Alternatively, as shown in FIG. 3B, measurement processing device 11 and operation unit 2 may perform radio communication via a communication device 29. Thus, the measurement can be taken easily and conveniently. In this case, communication device 29 and operation unit 2 are connected via I/F 25. In this case, measurement processing device 11 may include therein a communication device (not shown) connected to I/F 15 to transmit information about the detected potential difference to communication device 29 or receive a control signal from communication device 29.

In FIG. 4, a subject 300 faces forward. As to the posture of subject 300 for taking the measurement, the subject may lie on the back with the face upward or may stand.

Referring to FIG. 4, electrode H1 is disposed at the right arm 301 of subject 300. Electrode H2 is disposed at the left arm 302 of subject 300. Electrode F1 is disposed at the right leg 304 of subject 300. Electrode F2 is disposed at the left leg 305 of subject 300. Electrode sheet 19 is a sheet which is substantially rectangular in shape for example and is disposed at the surface of an abdomen 303 of subject 300. Electrode sheet 19 is disposed such that the longitudinal direction of electrode sheet 19 corresponds to the right-to-left direction of abdomen 303.

Here, electrodes H1, H2, F2, F2 disposed at the upper and lower limbs may be of the type attached to the surface of the abdomen or clip-shaped.

Figure 5:
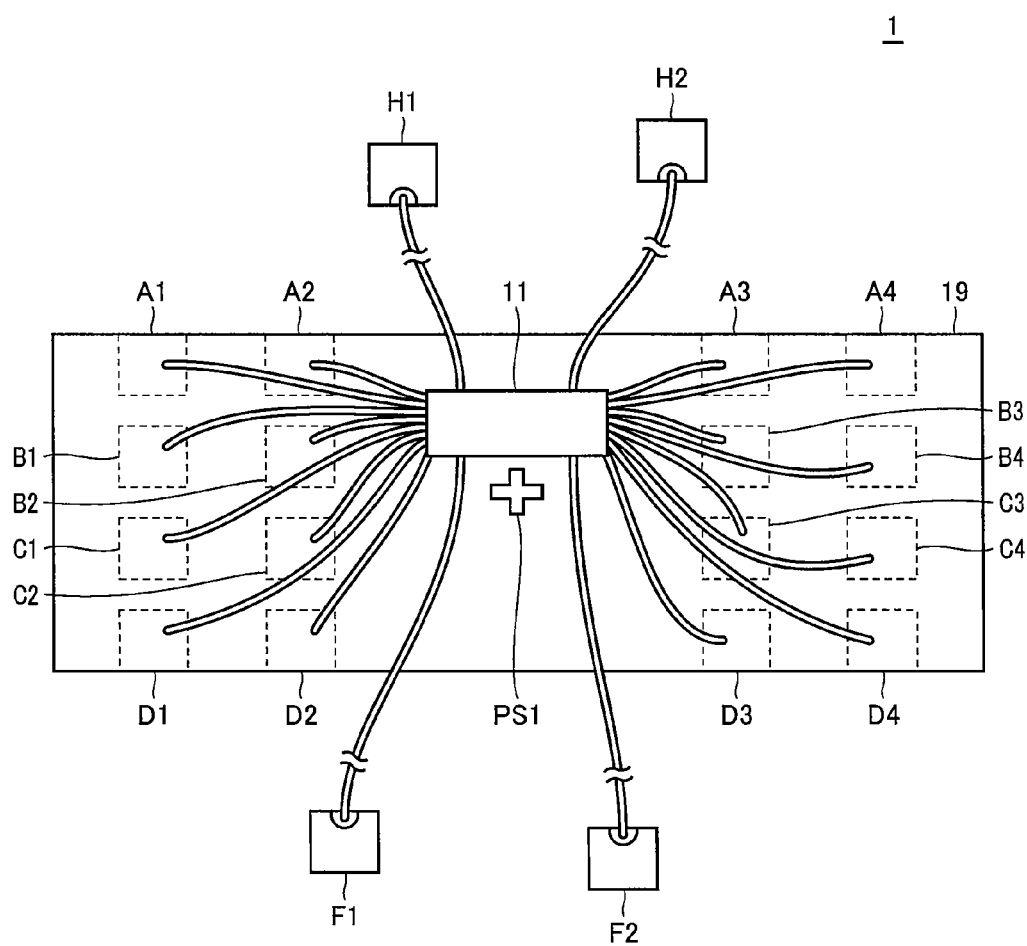
FIG. 5 is a schematic diagram of a measuring unit in the first embodiment of the present invention.

Referring to FIG. 5, to measurement processing device 11, a plurality of wires are connected for making electrical connection with respective electrodes that are components of electrode portion 10. Measurement processing device 11 and each electrode may be connected in advance or may be connected each time the measurement is taken.

Further, in order to make impedances of the wires uniform, the length and the thickness of each wire may be adjusted.

Figure 6:
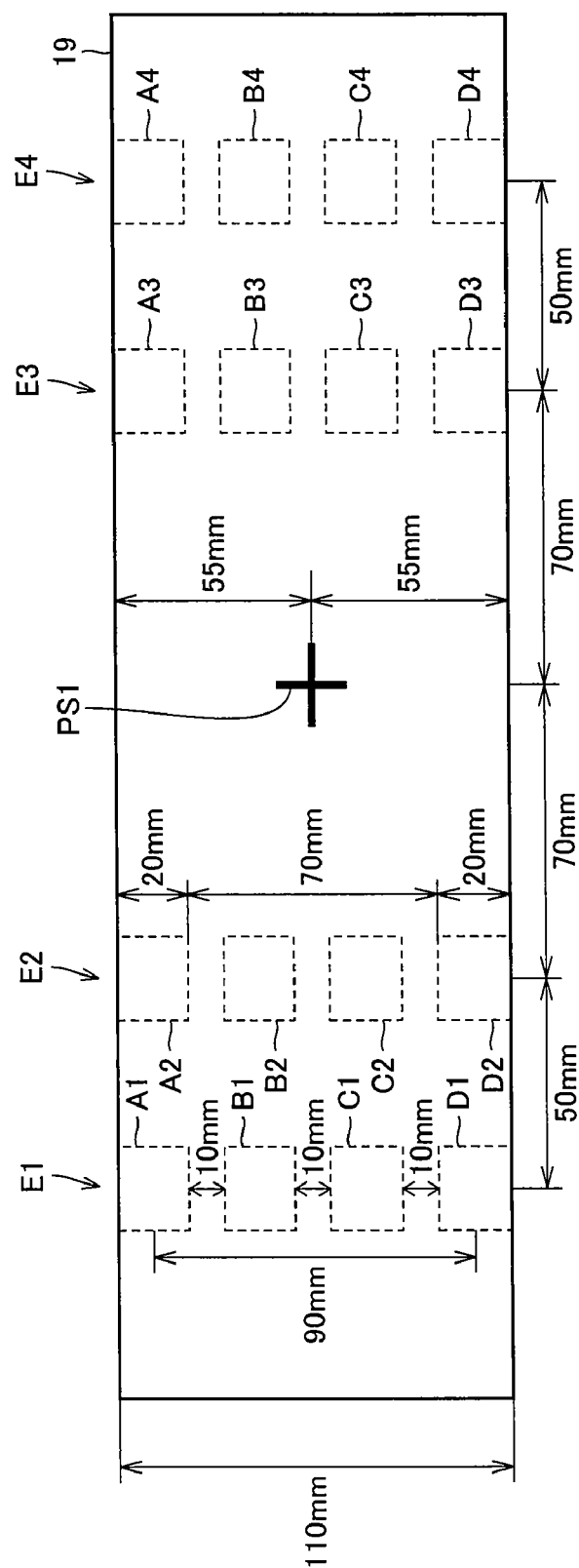
FIG. 6 is a diagram showing a specific example of the arrangement of an abdomen electrode portion of an electrode sheet.

As to the specific configuration of the electrode sheet:

Referring to FIG. 6, abdomen electrode row E1 is disposed linearly in the direction substantially perpendicular to the longitudinal direction of electrode sheet 19. Electrodes A1, D1 are disposed at respective positions sandwiching electrodes B1, C1. Likewise, other three abdomen electrode rows E2, E3, E4 are also disposed linearly in the direction substantially perpendicular to the longitudinal direction of electrode sheet 19, and electrodes A2 (A3, A4), D2 (D3, D4) are disposed at respective positions sandwiching electrodes B2 (B3, B4), C2 (C3, C4).

Electrode sheet 19 is transparent. Electrode sheet 19 includes a mark PS1 serving as positioning means corresponding to the navel position of subject 300. Mark PS1 is placed at the position (hereinafter referred to as "central position") relative to which the electrodes that are components of abdomen electrode portion 10.1 are symmetrical in the rightto-left direction and the top-to-bottom direction on electrode sheet 19. In the present embodiment, the central position is the position where a line which is parallel with the alignment direction of each abdomen electrode row E and which passes the middle point between abdomen electrode row E2 and abdomen electrode row E3 and a line which is perpendicular to the alignment direction of each abdomen electrode row E and which passes the middle point between electrode B2 (B3) and electrode C2 (C3) cross each other. Mark PS1 is a mark in the shape of a cross for example.

Thus, since mark PS1 is provided on electrode sheet 19, the position of the sheet to be laid against the navel of the subject can be easily identified. Further, electrode sheet 19 can be easily attached to the abdomen of the subject. Furthermore, since the above-described correlation formulas are defined using a reference which is determined with the navel position at the center, the measurement accuracy can be improved by correctly disposing the sheet relative to the navel position. In addition, the body fat can be stably measured. Here, the shape and the size of mark PS1 are not limited to specific ones. Further, the position where mark PS1 is placed is not necessarily limited to the central position.

Preferably, measurement processing device 11 is disposed in the vicinity of the central position of electrode sheet 19. Thus, the influence of the weight of measurement processing device 11 can be distributed uniformly to the right and left of the abdomen.

Each of electrodes A (A1, ..., A4), B (B1, ..., B4), C (C1, ..., C4) and D (D1, ..., D4) includes a first surface contacting the surface of the abdomen of the subject and a second surface opposite to the first surface. The second surface of the electrodes each has a square shape of 20 mm×20 mm for example. In each row, the distance between electrode A and electrode B, the distance between electrode B and electrode C, and the distance between electrode C and electrode D are each 10 mm for example. The distance between the central point of electrode A and the central point of electrode D is 90 mm for example. The distance between the central point of electrode A1 (B1, C1, D1) and the central point of electrode A2 (B2, C2, D2) is 50 mm for example. Likewise, the distance between the central point of electrode A3 (B3, C3, D3) and the central point of electrode A4 (B4, C4, D4) is 50 mm for example.

The dimension of the shorter side of electrode sheet 19 is 110 mm for example. Mark PS1 is provided at a substantially central position of electrode sheet 19. The distance between the line extending from the position where mark PS1 is provided perpendicularly to the longer side and the line extending through the central point of electrode A2 (B2, C2, D2) perpendicularly to the longer side is 70 mm for example. Likewise, the distance between the line extending from the position of mark PS1 normally to the longer side and the line extending through the central point of electrode A3 (B3, C3, D3) normally to the longer side is also 70 mm for example.

With the above-described positional relations, the electrodes are arranged on electrode sheet 19. Therefore, electrode sheet 19 may be merely attached to the surface of the abdomen of the subject to allow those electrodes to be disposed at respective positions defined on the surface of the abdomen of the subject. In other words, the four electrodes A, ..., D included in abdomen electrode row E are disposed at the surface of the abdomen in the aliment direction which is the direction (hereinafter referred to as "lengthwise direction") substantially perpendicular to a cross section of the abdomen of the subject.

Further, since the electrodes are each disposed on electrode sheet 19, a user (such as doctor or subject) can easily and conveniently dispose each electrode at its predetermined position of the abdomen of the subject. Further, since the positional relation of the electrodes is fixed, the measurement accuracy can be improved.

The size of electrode sheet 19 and the specific distance between the electrodes as shown in FIG. 6 are merely an example and are not limited to them. For example, although respective distances between the electrodes in abdomen electrode row E are all 10 mm, the distances may not be uniform as shown. Further, the shape of each electrode is not limited to rectangle and may be circle for example.

Figure 7:
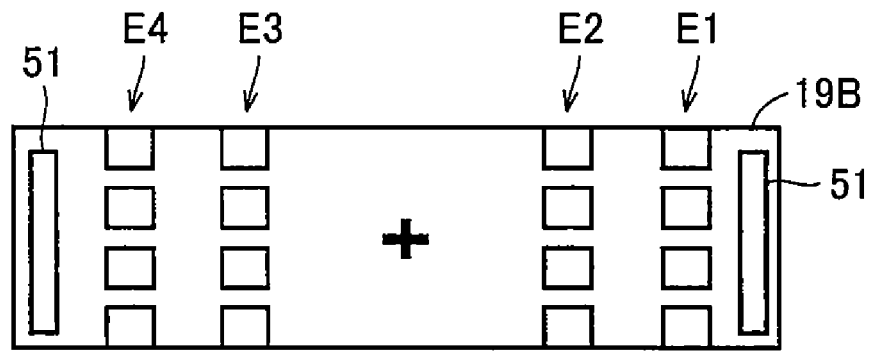
FIG. 7 shows the rear side of the electrode sheet.

Preferably, an adhesive sheet is provided on the rear surface (the surface touching the abdomen of the subject) of electrode sheet 19. As seen from the rear side, referring to FIG. 7, adhesive sheets 51 are respectively provided near the opposing ends in the longitudinal direction of electrode sheet 19 and are located closer to the opposing ends relative to abdomen electrode rows E1, E4. Since adhesive sheets 51 are attached near the opposing ends, abdomen electrode portion 10.1 is allowed to touch the abdomen more sufficiently, regardless of the shape of the abdomen. The accuracy of measurement can thus be improved. Here, although the example is illustrated here where adhesive sheets 51 are provided near the opposing ends in the longitudinal direction of electrode sheet 19, the sheets may be provided at any positions other than those near the opposing ends in the longitudinal direction. Further, although one adhesive sheet 51 is provided near each end to extend from one longer side to the other longer side, a plurality of dot-shaped adhesive sheets may be provided from one longer side to the other longer side. Furthermore, at least one additional adhesive sheet may be provided along the longer side of electrode sheet 19.

In the present embodiment, the electrodes that are components of abdomen electrode portion 10.1 are described here as those secured to the sheet material in advance. The electrodes, however, may not be secured to the sheet material. Namely, the electrodes that are components of abdomen electrode portion 10.1 may be disposed at respective predetermined positions with respect to the position of the navel of the subject as described above.

Further, although the shape of electrode sheet 19 is described here as substantially rectangular, the shape is not limited to such a shape and may be ellipse or square for example. In addition, although the shorter side of electrode sheet 19 is described here as the side parallel to the alignment direction of abdomen electrode row E, the longer side may be a side parallel with the alignment direction of abdomen electrode row E. In any case, a plurality of electrodes that are components of abdomen electrode portion 10.1 may be arranged in rows and columns and separated from each other with a predetermined distance therebetween.

Although the above-described example uses mark PS1 as an index for identifying the position corresponding to the navel position of the subject (hereinafter referred to as "position identifying index"), the mark is not limited to such a mark in the example.

Figure 8:
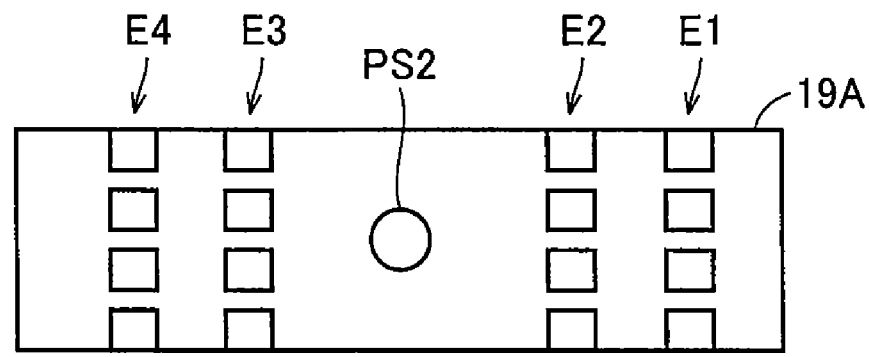
FIG. 8 shows an example of a position identifying index at an opaque electrode sheet.

As to an example of the position identifying index on an opaque electrode sheet, referring to FIG. 8, opaque electrode sheet 19A includes a hole PS2 located at a substantially central position and passing through the sheet from the front surface to the rear surface. Thus, a doctor or subject can see the navel of the subject through hole PS2 and the sheet can be positioned easily. Although the shape of hole PS2 is circular for example, the shape is not limited to a particular one. Such a hole PS2 may be provided in transparent electrode sheet 19. Further, the hole may not necessarily pass through the sheet, and the hole may be any which allows the navel of the subject to be confirmed through hole PS2.

Figure 9A:
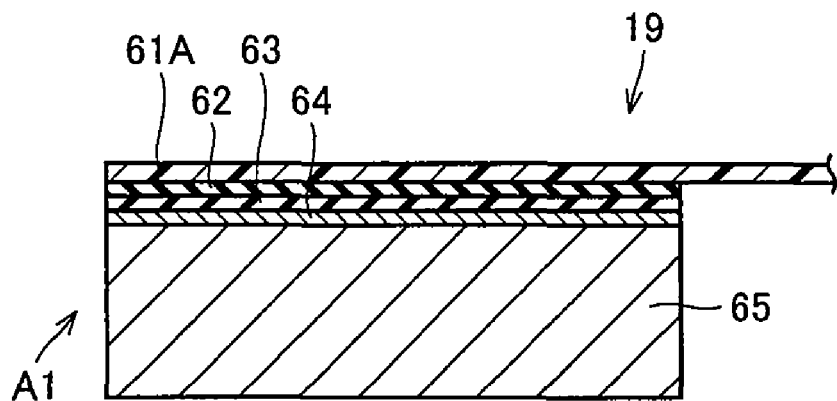
FIG. 9A is a cross-sectional view of a transparent electrode sheet.
Figure 9B:
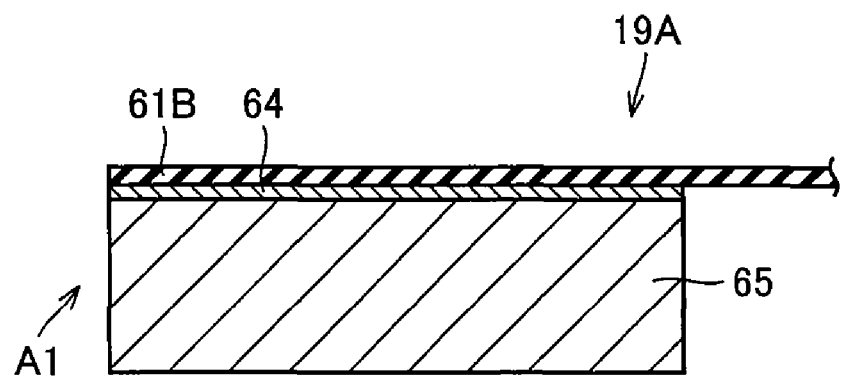
FIG. 9B is a cross-sectional view of an opaque electrode sheet.

With reference to FIGS. 9A and 9B, an example of the configuration of electrode sheets 19, 19A will be described.

FIG. 9A is a cross section of electrode sheet 19 including electrode A1. Referring to FIG. 9A, (transparent) electrode sheet 19 includes, as its components, a sheet material layer 61A, an adhesive material layer 62, an electrode base layer 63, an electrode layer 64 and a gel layer 65 arranged in the thickness direction successively in this order from the front surface. Namely, the electrode and gel that are components of electrode A1 are secured to the sheet material with the adhesive material and the electrode base material therebetween.

Sheet material layer 61A is made for example of polyvinyl chloride. As the material for adhesive material layer 62, an acrylic adhesive sheet is used for example. As the material for electrode base layer 63, a polyester film is used for example. Electrode layer 64 is formed for example with a silver-silver chloride electrode, or carbon electrode. Gel layer 65 is made of a highly electrically conductive material and is formed for example by compounding an acrylic resin with glycerol, water and sodium chloride.

FIG. 9B is a cross section of electrode sheet 19A including electrode A1. Referring to FIG. 9B, (opaque) electrode sheet 19A includes, as its components, a sheet material layer 61B, an electrode layer 64 and a gel layer 65 arranged successively in the thickness direction in this order from the front surface. Namely, the electrode and the gel that are components of electrode A1 are directly formed at the sheet material. Electrode A1 is thus formed by for example the vapor deposition or sputtering method without an adhesive layer. Here, although the example here shows electrode A1 formed without the adhesive material and the base material, the electrode may be formed with the adhesive material without the base material. Like electrode sheet 19, electrode sheet 19A may have electrode A1 secured to the sheet material with both of the adhesive material and the electrode base material therebetween.

Although FIGS. 9A and 9B are described using electrode A1 as a representative one, the cross sectional structure of electrode sheets 19, 19A including another electrode included in abdomen electrode portion 10.1 is similar to the above-described one.

<Operation of Body Fat Measuring Device>

Figure 10:
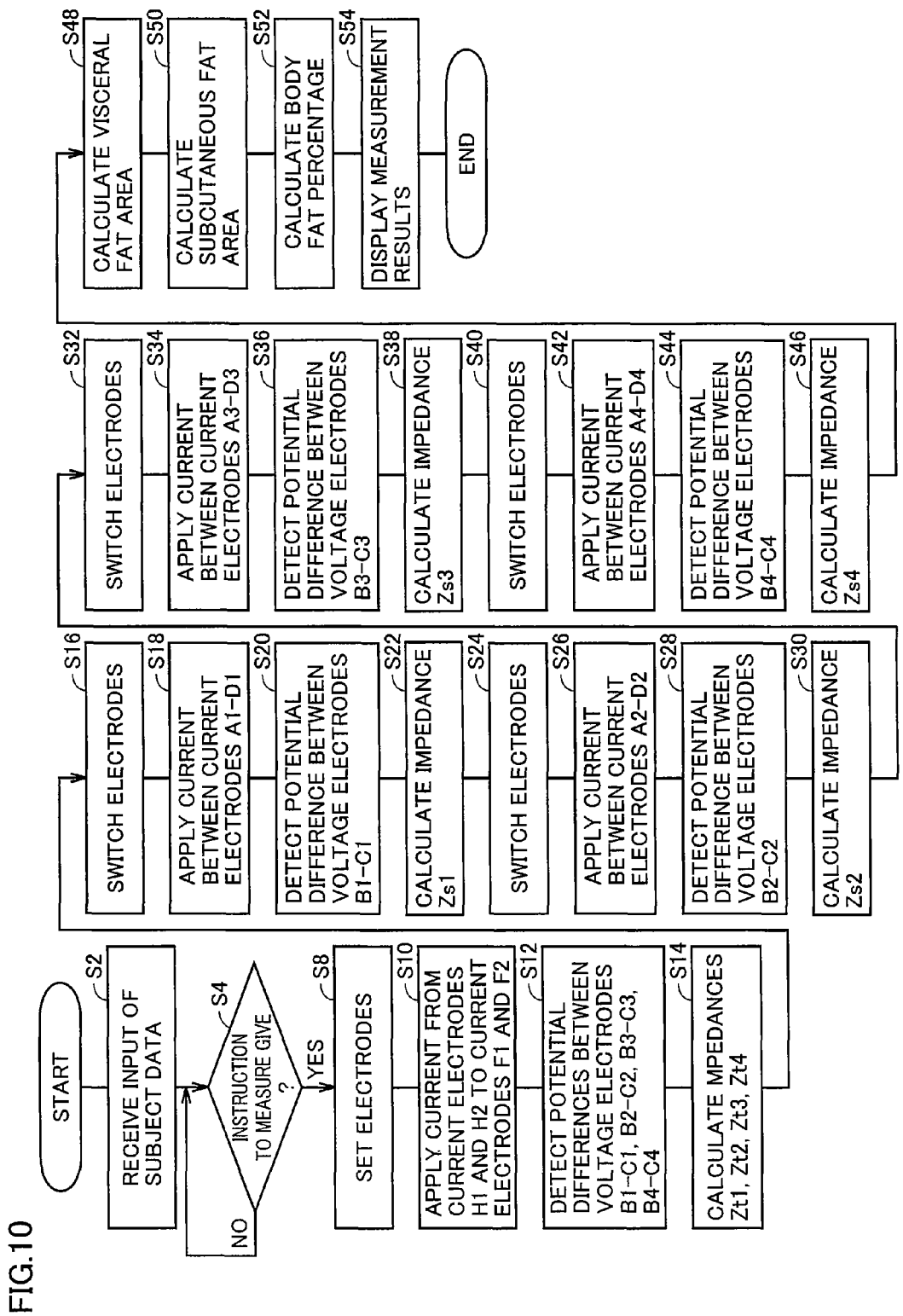
FIG. 10 is a flowchart showing a body fat measuring process in the first embodiment of the present invention.

The body fat measuring process in the first embodiment of the present invention as illustrated in the flowchart of FIG. 10 is stored in advance in storage portion 27 as a program, and operation processing portion 26 reads and executes the program to implement the function of the body fat measuring process.

Referring to FIG. 10, operation processing portion 26 receives input of subject data including physical data (waist length) (step S2). The subject data received here is temporarily recorded for example in storage portion 27.

Then, it is determined whether or not an instruction to start measurement is given (step S4). Operation processing portion 26 waits until the instruction to start measurement is given (NO in step S4). Detecting the instruction to start measurement (YES in S4), operation processing portion 26 sets electrodes (step S8). More specifically, operation processing portion 26 controls terminal switching portion 14 to connect two pairs of electrodes H1, H2, F1, F2 as electrodes for current to constant current generating portion 12. Further, operation processing portion 26 controls terminal switching portion 14 to connect the pair of electrodes B1, C1 as electrodes for voltage to voltage detecting portion 13.

Subsequently, operation processing portion 26 controls constant current generating portion 12 to apply a constant current from electrodes H1 and H2 to electrodes F1 and F2 (step S10). In this state, operation processing portion 26 causes voltage detecting portion 13 to detect a potential difference between electrodes B1 and C1, a potential difference between electrodes B2 and C2, a potential difference between electrodes B3 and C3 and a potential difference between electrodes B4 and C4 (step S12). In step S12, the electrodes for voltage are switched successively to the pair of electrodes B2, C2, the pair of electrodes B3, C3 and the pair of electrodes B4, C4.

In step S10, when the current is flown in the direction from the upper limbs to the lower limbs, it is preferable to short-circuit electrodes H1 and H2 and short-circuit electrodes F1 and F2. Further, in step S10, current may be applied from one of electrodes H1 and H2 to one of electrodes F1 and H2.

Impedance calculating portion 261 calculates impedances $Zt1$, $Zt2$, $Zt3$, $Zt4$ based on respective potential differences detected in step S12 (S14). Respective values of impedances $Zt1$, ..., $Zt4$ calculated here are temporarily recorded for example in storage portion 27.

Then, operation processing portion 26 switches the electrodes (step S16). More specifically, operation processing portion 26 controls terminal switching portion 14 to switch the electrodes for current from electrodes H1, H2, F1, F2 to electrodes A1, D1. Thus, terminal switching portion 14 disconnects electrodes H1, H2, F1, F2 and constant current generating portion 12 from each other and connects electrodes A1 and D1 and constant current generating portion 12 to each other. Operation processing portion 26 controls terminal switching portion 14 to switch electrodes for voltage from electrodes B4, C4 to electrodes B1, C1. Thus, terminal switching portion 14 disconnects electrodes B4, C4 and voltage detecting portion 13 from each other and connects electrodes B1, C1 to voltage detecting portion 13 to each other.

Subsequently, operation processing portion 26 causes constant current generating portion 12 to apply current between electrodes A1 and D1 (step S18). In this state, operation processing portion 26 causes voltage detecting portion 13 to detect the potential difference between electrodes B1 and C1 (step S20). Based on the potential difference detected in step S20, impedance calculating portion 261 calculates impedance $Zs1$ (step S22). The value of impedance $Zs1$ calculated here is temporarily recorded for example in storage portion 27.

Then, operation processing portion 26 switches the electrodes (step S24). More specifically, the operation processing portion controls terminal switching portion 14 to switch the electrodes for current from electrodes A1, D1 to electrodes A2, D2. Thus, terminal switching portion 14 disconnects electrodes A1, D1 and constant current generating portion 12 from each other and connects electrodes A2, D2 and constant current generating portion 12 to each other. Further, operation processing portion 26 controls terminal switching portion 14 to switch the electrodes for voltage from electrodes B1, C1 to electrodes B2, C2. Thus, terminal switching portion 14 disconnects electrodes B1, C1 and voltage detecting portion 13 from each other and connects electrodes B2, C2 and voltage detecting portion 13 to each other.

Subsequently, operation processing portion 26 causes constant current generating portion 12 to apply current between electrodes A2 and D2 (step S26). In this state, operation processing portion 26 causes voltage detecting portion 13 to detect the potential difference between electrodes B2 and C2 (step S28). Based on the potential difference detected in step S28, impedance calculating portion 261 calculates impedance Zs2 (step S30). The value of impedance Zs2 calculated here is temporarily recorded for example in storage portion 27.

Then, operation processing portion 26 switches the electrodes (step S32). More specifically, the operation processing portion controls terminal switching portion 14 to switch the electrodes for current from electrodes A2, D2 to electrodes A3, D3. Thus, terminal switching portion 14 disconnects electrodes A2, D2 and constant current generating portion 12 from each other and connects electrodes A3, D3 and constant current generating portion 12 to each other. Operation processing portion 26 controls terminal switching portion 14 to switch the electrodes for voltage from electrodes B2, C2 to electrodes B3, C3. Thus, terminal switching portion 14 disconnects electrodes B2, C2 and voltage detecting portion 13 from each other and connects electrodes B3, C3 and voltage detecting portion 13 to each other.

Subsequently, operation processing portion 26 causes constant current generating portion 12 to apply current between electrodes A3 and D3 (step S34). In this state, operation processing portion 26 causes voltage detecting portion 13 to detect the potential difference between electrodes B3 and C3 (step S36). Based on the potential difference detected in step S36, impedance calculating portion 261 calculates impedance Zs3 (step S38). The value of impedance Zs3 calculated here is temporarily recorded for example in storage portion 27.

Then, operation processing portion 26 switches the electrodes (step S40). More specifically, the operation processing portion controls terminal switching portion 14 to switch the electrodes for current from electrodes A3, D3 to electrodes A4, D4. Thus, terminal switching portion 14 disconnects electrodes A3, D3 and constant current generating portion 12 from each other and connects electrodes A4, D4 and constant current generating portion 12 to each other. Operation processing portion 26 controls terminal switching portion 14 to switch the electrodes for voltage from electrodes B3, C3 to electrodes B4, C4. Thus, terminal switching portion 14 disconnects electrodes B3, C3 and voltage detecting portion 13 from each other and connects electrodes B4, C4 and voltage detecting portion 13 to each other.

Subsequently, operation processing portion 26 causes constant current generating portion 12 to apply current between electrodes A4, D4 (step S42). In this state, operation processing portion 26 causes voltage detecting portion 13 to detect the potential difference between electrodes B4, C4 (step S44). Based on the potential difference detected in step S44, impedance calculating portion 261 calculates impedance Zs4 (step S46). The value of impedance Zs4 calculated here is temporarily recorded for example in storage portion 27.

Next, visceral fat amount calculating portion 262A calculates visceral fat area Sv from the physical data (waist length) which is input in step S2 and impedances Zt1, . . . , Zt4 and impedances Zs1, . . . , Zs4 (step S48). Visceral fat area Sv is calculated with the above-described formula (1). Here, in the case where four abdomen electrode rows E1, E2, E3, E4 are provided as done in the present embodiment, the average value of the four impedances Zt1, . . . , Zt4 may be substituted into correlation formula (1) for impedance Zt and the average value of the four impedances Zs1, . . . , Zs4 may be substituted into correlation formula (1) for impedance Zs.

Simultaneously, subcutaneous fat amount calculating portion 262B calculates subcutaneous fat area Ss from the physical data (waist length) which is input in step S2 and impedances Zs1, . . . , Zs4 (step S50). Subcutaneous fat area Ss is calculated with the above-described formula (2). Here, in this case as well, the average value of the four impedances Zs1, . . . , Zs4 may be substituted into correlation formula (2) for impedance Zs.

Further, body fat amount calculating portion 262C calculates the body fat percentage based on the subject data (height, weight) of the subject that is input in step S2 and impedances Zt1, . . . , Zt4 (step S52). The body fat percentage is calculated with the above-described formulas (3) and (4). In this case as well, the average value of the four impedances Zt1, . . . , Zt4 may be substituted into correlation formula (4) for impedance Zt.

Finally, operation processing portion 26 displays the results of measurement on display portion 21 (step S54).

After the above-described steps, the body fat measuring process in the first embodiment of the present invention is ended.

Here, impedances Zt1, . . . , Zt4 each have a typical value of approximately $5\Omega$. Impedances Zs1, . . . , Zs4 each also have a typical value of approximately $80\Omega$.

As described above, both of the two types of impedances Zt, Zs are calculated based on the potential difference between electrodes B and C which are disposed in the lengthwise direction of the abdomen of the subject. Thus, the difference in degree of curve between electrodes between subjects who differ from each other in shape of the abdomen (the degree of projection in the direction parallel to the cross section of the abdomen) is smaller and thus differences of the range and sensitivity of the detection of the potential difference between subjects due to the difference in degree of curve can be reduced. Further, variation of the potential difference due to variation of the electrode positions in the direction parallel to the cross section of the abdomen caused while the subject is breathing can be reduced. Thus, the measurement accuracy can be improved.

Further, since a plurality of abdomen electrode rows E1, E2, E3, E4 are provided to average a plurality of potential differences, the influences of the distribution of the fat and the thickness of the fat can be eliminated.

Although the above-described flowchart shows that the impedance is calculated each time the potential difference is detected. Alternatively, the impedances may be calculated all together after all potential differences are calculated. Further, the order in which the setting and switching of the electrodes and the detection of the potential differences are done is not limited to the above-described order. In other words, the order of steps S8 to S14, steps S16 to S22, steps S24 to S30, steps S32 to S38 and steps S40 to S46 may be any order.

Further, in the step of calculating the body fat, impedances Zt1, . . . , Zt4 and impedances Zs1, . . . , Zs4 are averaged. The method, however, is not limited to the above-described one. Based on the average value of a plurality of potential differences detected by flowing current from the four limbs, impedance Zt may be calculated and, based on the average value of a plurality of potential differences detected by flowing current from the abdomen, impedance Zs may be calculated.

Here, although impedances Zt1, . . . , Zt4 and impedances Zs1, . . . , Zs4 are averaged for use in calculating the visceral fat amount and the subcutaneous fat amount for example, any operation other than the averaging operation may be performed. For example, a correlation formula may be provided for each impedance to calculate the visceral fat amount and the subcutaneous fat amount for example.

Further, in the present embodiment, as the body fat of the subject, the visceral fat amount (visceral fat area), the subcutaneous fat amount (subcutaneous fat area) and the body fat amount (body fat percentage) are calculated. At least the visceral fat amount, however, may be calculated. In this case, in step S2, only the physical data (waist length) may be input.

Figure 11:
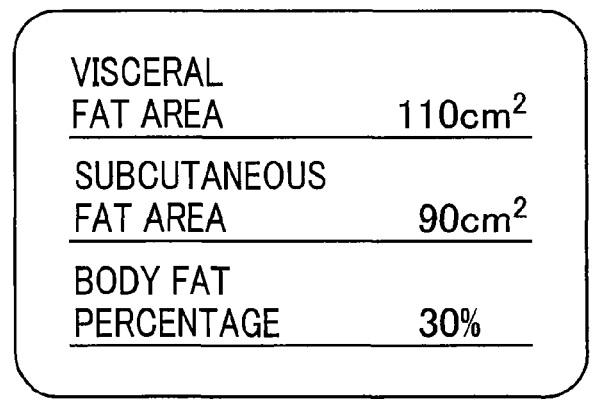
FIG. 11 shows an example where measurement results are displayed.

As to examples of display:

FIG. 11 illustrates an example of display of measurement results in step S54 of FIG. 10. Referring to FIG. 11, display portion 21 indicates "visceral fat area 110 cm$^2$," "subcutaneous fat area 90 cm$^2$" and "body fat percentage 30%" in respective predetermined regions where the calculated values are indicated as numerical values. Thus, the subject and/or doctor can know the specific numerical values of the visceral fat area, subcutaneous fat area and body fat percentage of the subject. Further, since these values are indicated simultaneously, the fat balance of the subject can further be known.

Figure 12A:
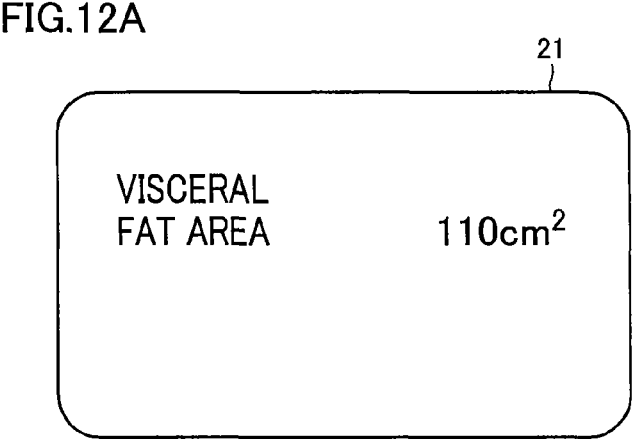
FIG. 12A shows an example where only a visceral fat area is displayed.
Figure 12B:
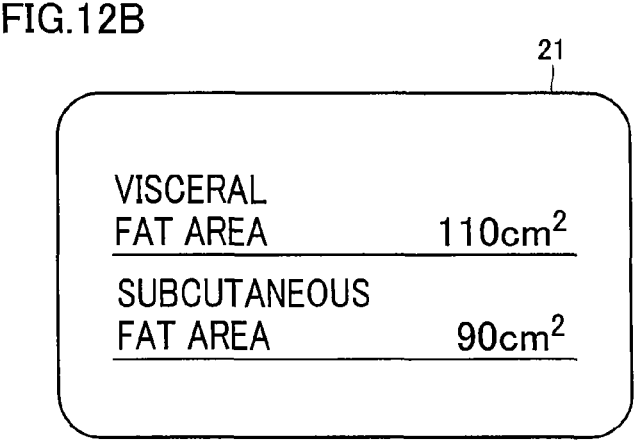
FIG. 12B shows an example where a visceral fat area and a subcutaneous fat area are displayed.

Here, the display is not limited to the example as shown in FIG. 11, and only the visceral fat area may be indicated as a result of measurement as shown in FIG. 12A, or the visceral fat area and the subcutaneous fat area may be indicated as results of measurement as shown in FIG. 12B.

The subject data may further be indicated in addition to the results of measurement.

FIG. 13A shows a first diagram indicating, as subject data, the waist length which is physical data and additionally data such as patient ID, age, gender, height and weight for example. As the results of measurement, the visceral fat area, subcutaneous fat area and body fat percentage are indicated.

FIG. 13B shows a second diagram which also indicates, as subject data, the waist length which is physical data and additionally data such as patient ID, age, gender, height and weight for example. As the results of measurement, the visceral fat area and subcutaneous fat area are indicated.

When the results of measurement are indicated, a reference value of the visceral fat area may further be indicated. "Reference value of the visceral fat area" refers to the reference value used by the Japan Society for the Study of Obesity as a criterion for making a judgment about visceral obesity, and is specifically 100 cm$^2$.

Figures 14, 15:
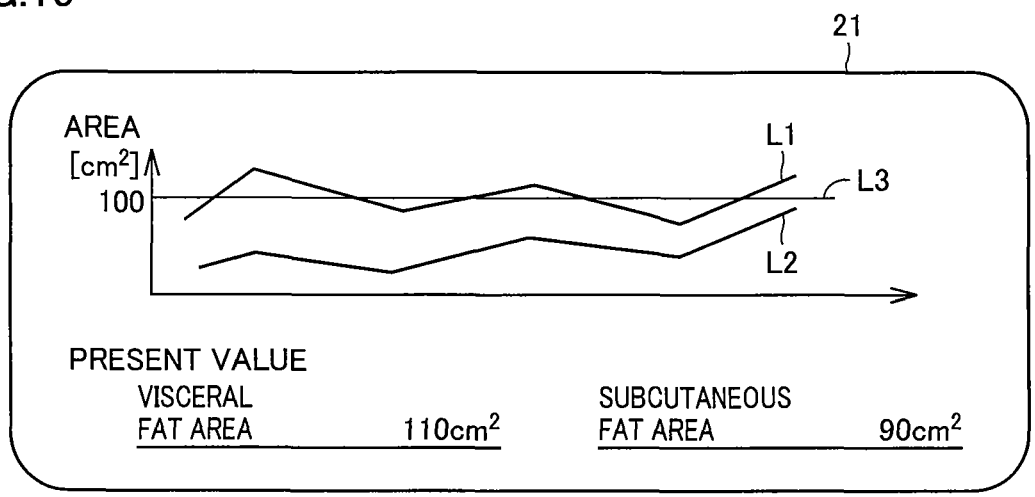
FIG. 14 is a diagram showing an example where a reference value of the visceral fat area is further displayed together with measurement results.
FIG. 15 is a diagram showing an example of the case where measured values taken in the past are displayed in the form of a graph together with measurement results.

FIG. 14 is a diagram showing an example where the reference value of the visceral fat area is additionally indicated. Referring to FIG. 14, display portion 21 indicates the results of measurement similarly to FIG. 11 and additionally indicates the reference value (100 cm$^2$) of the visceral fat area at a side of the measured value (110 cm$^2$) of the visceral fat area. Thus, since the reference value of the visceral fat area is indicated together with the measured value thereof, the subject and/or doctor can easily know whether the subject is classified into the visceral obesity which is considered as the one having a high risk of lifestyle related diseases. Further as shown in FIG. 14, at a side of the measured value (30%) of the body fat percentage, its standard value (10-20% for example) may be additionally indicated.

In addition to the results of measurement, the values measured in the past may be indicated in the form of a graph. Referring to FIG. 15, display portion 21 indicates a graph showing a course (transition) of the measured values, with the vertical axis for the area (unit: cm$^2$) and the horizontal axis for the time. In this case, the reference value (100 cm$^2$) of the visceral fat area may be indicated additionally. In this diagram, bent line L1 shows a course of measured values of the visceral fat area in the past, and bent line L2 shows a course of measured values of the subcutaneous fat area in the past. Straight line L3 which is parallel with the horizontal axis is a reference line indicating the reference value of the visceral fat area. Although the information about the visceral fat area and the subcutaneous fat area is displayed here, only the information about the visceral fat area may be displayed. Further, the graph of bent line L1 concerning the visceral fat area and the graph of bent line L2 concerning the subcutaneous fat area may be indicated separately.

In the above-described first embodiment, of electrodes A, B, C, D included in abdomen electrode row E (E1, E2, E3, E4), the pair of electrodes B, C located on the inner side is used as electrodes for voltage commonly to the case where current is flown from the four limbs and the case where the current is flown at the abdomen. The electrodes, however, may not be used commonly to these cases. For example, in the case where the current is flown from the four limbs, any pair of electrodes other than the pair of electrodes B, C may be used as electrodes for voltage. For example, the pair of electrodes A, D located on the outer side may be used, which is desirable in terms of accurate measurement of the value since the measured value is larger. Alternatively, the pair of electrodes A, B or the pair of electrodes B, D may also be used.

Further, in the present embodiment, of the four electrodes A, B, C, D, the pair of electrodes A, D located on the outer side is used to function as electrodes for current and the pair of electrodes B, C located on the inner side is used to function as electrodes for voltage. Alternatively, these pairs may be used vice versa. Namely, the pair of electrodes A, D may be used to function as electrodes for voltage and the pair of electrodes B, C may be used to function as electrodes for current.

Furthermore, although abdomen electrode row E includes four electrodes A, B, C, D here, a pair of electrodes arranged in the same alignment direction may be included additionally. In this case, in steps S18, S26, S34, S42, the pair of electrodes located on the outermost side among the six electrodes is used for applying current via the pair of electrodes. In this state, respective potential differences of the two pairs of electrodes located on the inner side are detected (step S20, S28, S36, S44). In the case where current is flown from the four limbs, the potential difference between the electrodes of the two pair located on the inner side are detected respectively for each row. The detected two potential differences may be averaged to calculate each impedance for each row. Here, the detected two potential differences may have been averaged at the time when the body fat is calculated.

Moreover, in the present embodiment, the impedance is calculated from the detected potential differences and the visceral fat amount for example is calculated based on the calculated impedance. The visceral fat amount for example, however, may be directly calculated from the detected potential differences. Namely, although the above-descried correlation formula (1) uses the two types of impedances Zt, Zs, the formula may use two types of potential differences.

Second Embodiment

A description will now be given of a body fat measuring device according to a second embodiment of the present invention.

Body fat measuring device 100 in the first embodiment as described above includes measurement processing device 11 and operation unit 2 separately. The body fat measuring device in the second embodiment includes measurement processing device 11 and operation unit 2 as an integrated unit. In the following, differences between the second embodiment and the first embodiment will be described.

Figure 16:
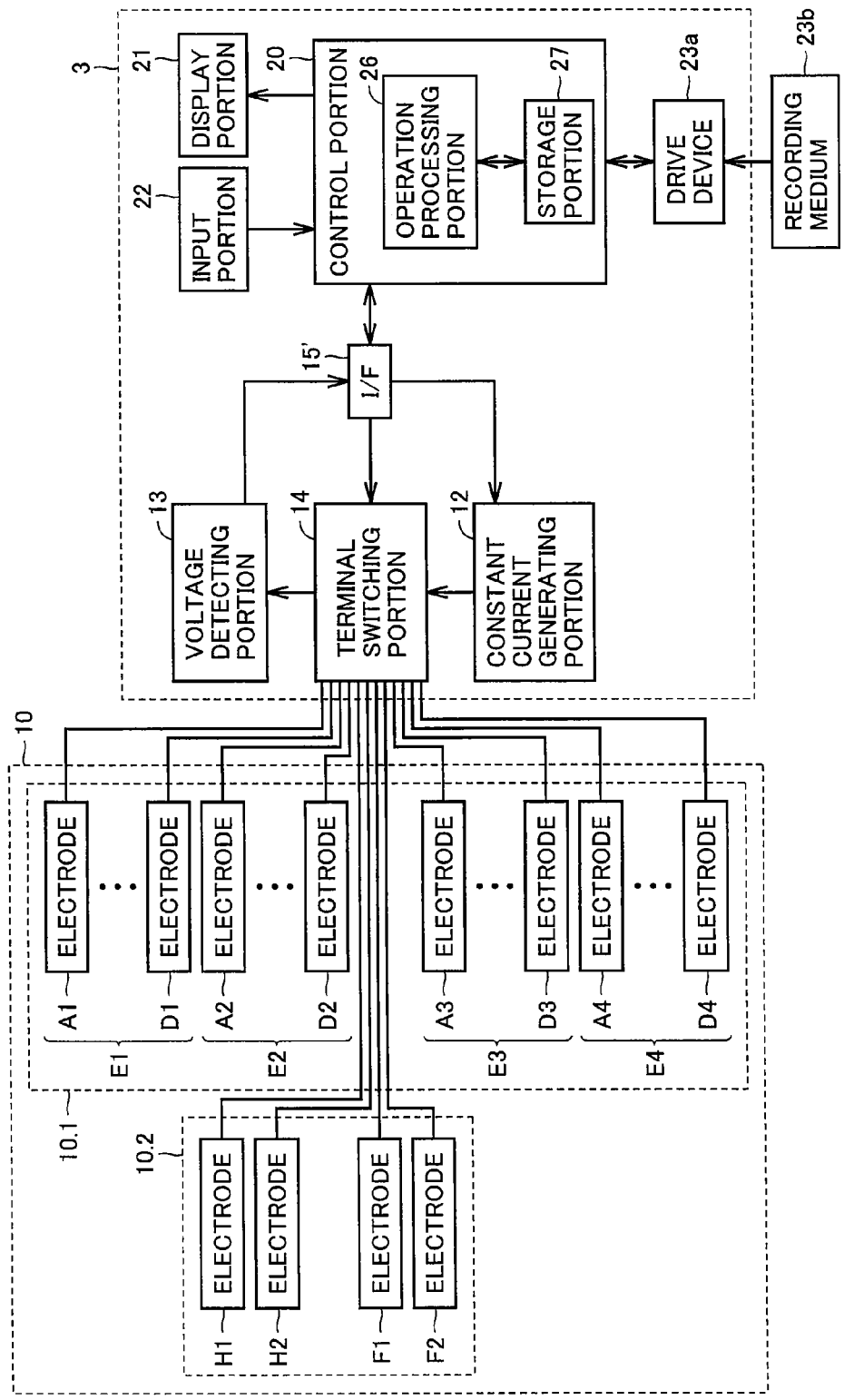
FIG. 16 shows a configuration of a body fat measuring device in a second embodiment of the present invention.

Referring to FIG. 16, body fat measuring device 200 includes an electrode portion 10 and a measurement operation device 3. Measurement operation device 3 includes a constant current generating portion 12, a voltage detecting portion 13, a terminal switching portion 14, an I/F 15', a control portion 20, a display portion 21, an input portion 22 and a drive device 23a.

I/F 15' is connected to constant current generating portion 12, voltage detecting portion 13, terminal switching portion 14 and control portion 20.

Figure 17:
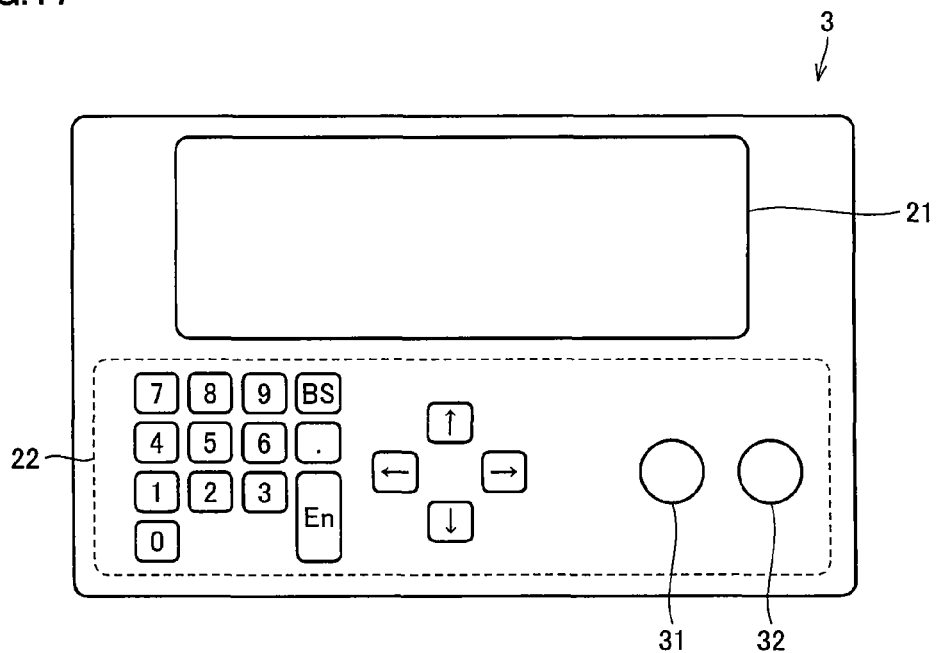
FIG. 17 is a schematic diagram showing an example of a measurement operation device of the body fat measuring device in the second embodiment of the present invention.

Referring to FIG. 17, body fat measuring device 200 in the second embodiment of the present invention includes display portion 21 and input portion 22 on the front surface of measurement operation device 3. Input portion 22 includes, for example, numeric keys, determination key, back space key and cursor keys for moving a cursor on the screen upward, downward, rightward and leftward. Input portion 22 includes a measurement start key 31 for giving an instruction to start measurement and a measurement stop key 32 for giving an instruction to stop the measurement.

Figure 18:
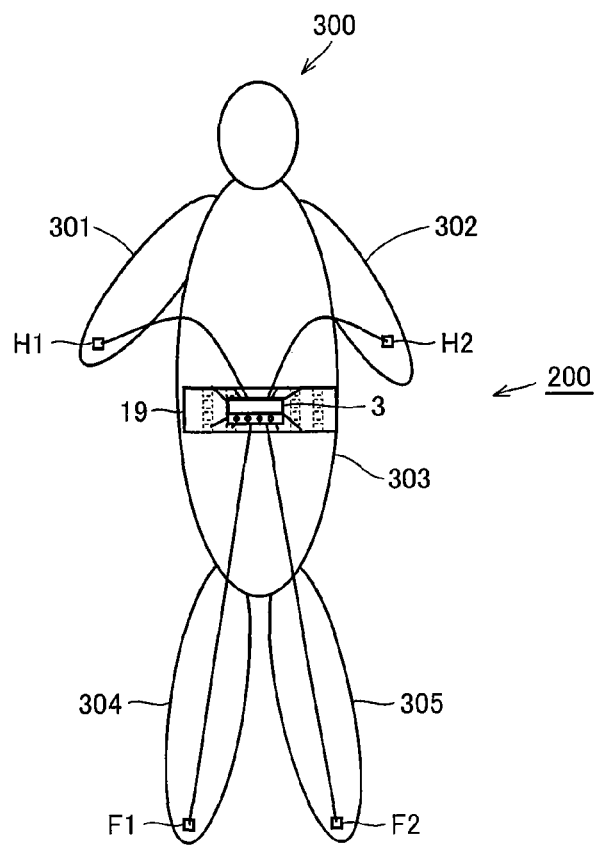
FIG. 18 shows how the body fat of a subject is measured using the body fat measuring device in the second embodiment of the present invention.

In FIG. 18 showing how the body fat of a subject is measured using body fat measuring device 200, subject 300 faces forward. As to the posture of the subject for taking measurement, the subject may lie on the back with the face upward or may stand.

As to measurement operation device 3, the front surface side of an electrode sheet 19 and the rear surface of measurement operation device 3 (the surface opposite to the front surface) are allowed to contact each other. Thus, with electrode sheet 19 placed on an abdomen 303 of subject 300, a doctor for example can confirm the results of measurement.

Figure 19:
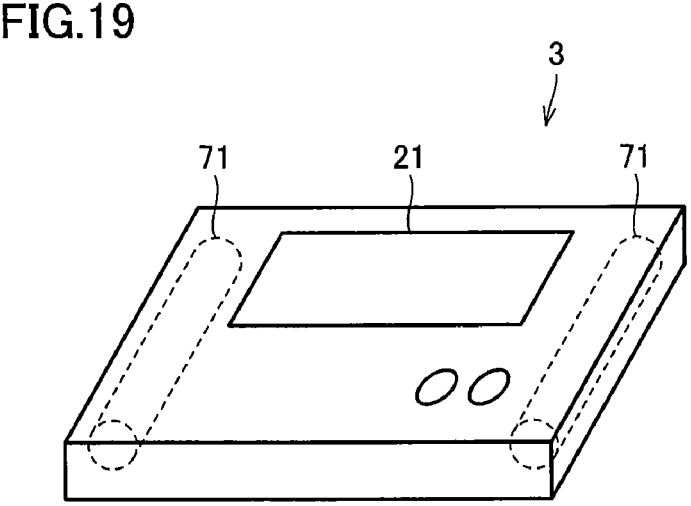
FIG. 19 shows an example where two batteries contained in the measurement operation device are arranged.

As shown in FIG. 19, two batteries 71 contained in measurement operation device 3 are preferably placed therein at respective positions at the same distances from the center of measurement operation device 3 in the right-to-left direction and the top-to-bottom direction. Thus, the weight balance of the body of measurement operation device 3 can be improved. Further, the thickness of measurement operation device 3 can be reduced (downsized). Here, since display portion 21 is positioned to equally extend in the right-to-left direction from the center of measurement operation device 3, the example is shown where batteries 71 are placed therein on the opposite sides of display portion 21 in the right-to-left direction. Here, the batteries are not limited to two batteries 71. One or three or more batteries may be contained in the manner that keeps the balance of measurement operation device 3.

Figure 20:
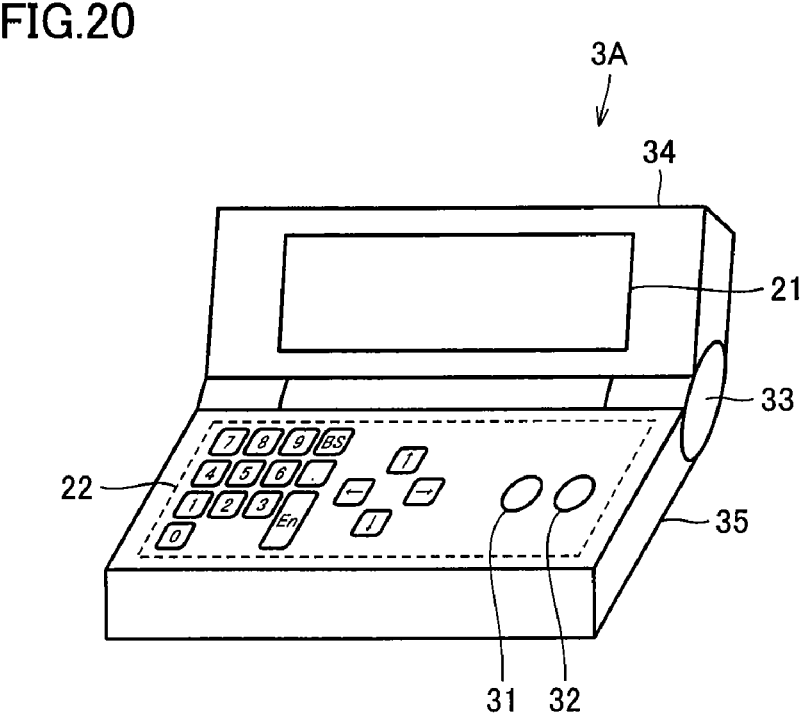
FIG. 20 is a schematic diagram showing another example of the measurement operation device of the body fat measuring device in the second embodiment of the present invention.

For allowing subject 300 to be able to easily confirm the results of measurement, measurement operation device 3 may be in the form as shown in FIG. 20. FIG. 20 shows the device as measurement operation device 3A since the form is different.

Referring to FIG. 20, in measurement operation device 3A, a hinge 33 is provided between a first housing 34 including display portion 21 and a second housing 35 including for example terminal switching portion 14 and input portion 22. The position and the shape of hinge 33 are not limited to particular ones. First housing 34 may be inclined to allow the subject to be able to confirm the results of measurement with its posture taken for measurement as it is. In this case, preferably first housing 34 is disposed on the leg side of the subject and second housing 35 is disposed on the head side of the subject.

A body fat measuring method performed by the body fat measuring device or operation unit of the present invention may be provided as a program. Such a program may be provided as a program product recorded on an optical media such as CD-ROM (Compact Disk-ROM) or a computer-readable recording medium such as memory card. The program may also be provided as the one downloaded via a network.

The provided program product is installed in a program storage unit such as hard disk and the installed program is executed. The program product here includes the program itself and the recording medium on which the program is recorded.

It should be understood that the embodiments disclosed herein are illustrative and non-restrictive in every respect. The scope of the invention is defined by the claims, rather than the description above, and is intended to include all modifications equivalent in meaning and scope to the claims.

The invention claimed is:

1. A body fat measuring device comprising:
   at least one pair of first electrodes configured to be disposed respectively at a first site and a second site, wherein the first site and the second site are located away from an abdomen of a subject, and said abdomen is located between the first site and the second site;
   an electrode group including a first abdomen electrode configured to be disposed at a surface of the abdomen of said subject,
   said first abdomen electrode including a pair of second electrodes and a pair of third electrodes disposed in an alignment direction substantially perpendicular to a cross section of said abdomen;
   an applying portion for alternately applying electric current to said subject via said first electrodes and said third electrodes;
   a detecting portion for alternately detecting a first potential difference between the pair of second electrodes when the electric current is applied via said first electrodes, and a second potential difference between the pair of second electrodes when the electric current is applied via said third electrodes; and
   a visceral fat amount calculating portion for calculating a visceral fat amount of said subject based on said detected first and second potential differences and physical data of said subject.

2. The body fat measuring device according to claim 1, wherein
   said third electrodes are disposed at respective positions sandwiching said second electrodes in said alignment direction.

3. The body fat measuring device according to claim 1, wherein
   said electrodes of said one predetermined pair are said second electrodes.

4. The body fat measuring device according to claim 1, wherein
   said electrodes of said one predetermined pair are electrodes that are included in said first abdomen electrode and that are electrodes of a pair other than the pair of said second electrodes.

5. The body fat measuring device according to claim 4, wherein
   said third electrodes are disposed at respective positions sandwiching said second electrodes in said alignment direction, and
   said electrodes of said one predetermined pair are said third electrodes.

6. The body fat measuring device according to claim 1, further comprising an impedance calculating portion for calculating two types of impedances based on said first potential difference and said second potential difference respectively, wherein
   said visceral fat amount calculating portion calculates said visceral fat amount based on said calculated two types of impedances and said physical data of said subject.

7. The body fat measuring device according to claim 6, wherein
said visceral fat amount calculating portion calculates said visceral fat amount using a predetermined correlation formula of a relation between said two types of impedances, said physical data and said visceral fat amount.

8. The body fat measuring device according to claim 1, further comprising a display portion for displaying said calculated visceral fat amount.

9. The body fat measuring device according to claim 1, further comprising a subcutaneous fat amount calculating portion for calculating a subcutaneous fat amount of said subject based on said detected second potential difference and said physical data of said subject.

10. The body fat measuring device according to claim 1, wherein
said physical data includes at least one of circumference of the abdomen, lateral width of the abdomen, thickness of the abdomen, height, and weight of said subject.

11. The body fat measuring device according to claim 1, wherein
said first site and said second site include an upper limb and a lower limb respectively.

12. The body fat measuring device according to claim 1, wherein
said electrode group further includes a second abdomen electrode,
said second abdomen electrode includes fourth electrodes and fifth electrodes disposed substantially parallel with said alignment direction and corresponding respectively to said second electrodes and said third electrodes,
said applying portion further applies electric current to said subject via said fifth electrodes,
said detecting portion further detects a third potential difference between said fourth electrodes in a case where electric current is applied via said fifth electrodes, and
said visceral fat amount calculating portion calculates said visceral fat amount by averaging said second potential difference and said third potential difference.

13. The body fat measuring device according to claim 1, wherein
said first abdomen electrode further includes a pair of sixth electrodes,
said detecting portion further detects a fourth potential difference between said sixth electrodes in said second case, and
said visceral fat amount calculating portion calculates said visceral fat amount by averaging said second potential difference and said fourth potential difference.

14. The body fat measuring device according to claim 1, wherein
said first abdomen electrode includes a first surface contacting the surface of said abdomen and a second surface opposite to said first surface, and
said body fat measuring device further comprises a sheet material where said second surface is fixed.

15. The body fat measuring device according to claim 14, wherein
said sheet material includes positioning means corresponding to a navel position of said subject.

16. The body fat measuring device according to claim 15, wherein
said positioning means is a mark placed at a predetermined position of said sheet material.

17. The body fat measuring device according to claim 15, wherein
said positioning means is a hole opened at a predetermined position of said sheet material.

18. A measuring unit controlled by an operation unit calculating a visceral fat amount, for measuring a potential difference generated at a body surface of a subject in a state where electric current is applied to said subject, said measuring unit comprising:
at least one pair of first electrodes configured to be disposed respectively at a first site and a second site, wherein the first site and the second site are located away from an abdomen of the subject, and said abdomen is located between the first site and the second site;
an electrode group including a first abdomen electrode configured to be disposed at a surface of the abdomen of said subject,
said first abdomen electrode including a pair of second electrodes disposed in an alignment direction substantially perpendicular to a cross section of said abdomen and a pair of third electrodes disposed at respective positions sandwiching said second electrodes in said alignment direction;
an applying portion for alternately applying electric current to said subject via said first electrodes and said third electrodes based on a signal from said operation unit;
a detecting portion for alternately detecting a first potential difference between the pair of second electrodes when the electric current is applied via said first electrodes, and for detecting a second potential difference between the pair of second electrodes when the electric current is applied via said third electrodes; and
a transmitting portion for transmitting to said operation unit data concerning said detected first and second potential differences.

19. A body fat measuring program product for controlling a measuring unit including an electric current applier for applying electric current to a subject and a detector for detecting a potential difference generated at a body surface of said subject in a state where the electric current is applied to said subject, and causing a computer to execute a body fat measuring process based on a result of measurement by said measuring unit, said body fat measuring program product causing the computer to execute the steps of:
causing said electric current applier to apply electric current via at least one pair of out-of-abdomen electrodes disposed away from an abdomen of said subject and sandwiching said abdomen;
causing said detector to detect a first potential difference between a pair of second abdomen electrodes that is one predetermined pair among four electrodes disposed at a surface of said abdomen and disposed in an alignment direction substantially perpendicular to a cross section of said abdomen, when the electric current is applied via said out-of-abdomen electrodes;
causing said electric current applier to apply electric current via a pair of first abdomen electrodes located on an outer side among said four electrodes;
causing said detector to alternately detect a second potential difference between the pair of second abdomen electrodes when the electric current is applied via said first abdomen electrodes;
obtaining said detected first and second potential differences; and
calculating a visceral fat amount of said subject based on said obtained first and second potential differences and physical data of said subject.

20. A method of controlling a body fat measuring device by controlling a measuring unit including an electric current applier for applying electric current to a subject and a detector for detecting a potential difference generated at a body surface of said subject in a state where the electric current is applied to said subject, for causing said body fat measuring device including said measuring unit to execute a body fat measuring process, the method comprising the steps of:

- causing said electric current applier to apply electric current via at least one pair of out-of-abdomen electrodes disposed away from an abdomen of said subject and sandwiching said abdomen;
- causing said detector to detect a first potential difference between a pair of second abdomen electrodes that is one predetermined pair among four electrodes disposed at a surface of said abdomen and disposed in an alignment direction substantially perpendicular to a cross section of said abdomen, when the electric current is applied via said out-of-abdomen electrodes;
- causing said electric current applier to apply electric current via a pair of first abdomen electrodes located on an outer side among said four electrodes;
- causing said detector to alternately detect a second potential difference between the pair of second abdomen electrodes when the electric current is applied via said first abdomen electrodes;
- obtaining said detected first and second potential differences; and
- calculating a visceral fat amount of said subject based on said obtained first and second potential differences and physical data of said subject.

* * * * *